(12) United States Patent
Miyata

(10) Patent No.: US 11,564,924 B2
(45) Date of Patent: Jan. 31, 2023

(54) PHARMACEUTICAL COMPOSITION FORMED BY COMBINING PYRIDOXAMINE COMPOUND AND THIAMINE COMPOUND

(71) Applicant: RENASCIENCE CO., LTD., Tokyo (JP)

(72) Inventor: Toshio Miyata, Miyagi (JP)

(73) Assignee: RENASCIENCE CO., LTD., Tokyo (JP)

(*) Notice: Subject to any disclaimer, the term of this patent is extended or adjusted under 35 U.S.C. 154(b) by 155 days.

(21) Appl. No.: 16/935,400

(22) Filed: Jul. 22, 2020

(65) Prior Publication Data

US 2021/0000829 A1 Jan. 7, 2021

Related U.S. Application Data

(63) Continuation of application No. 15/507,057, filed as application No. PCT/JP2015/073935 on Aug. 26, 2015, now abandoned.

(30) Foreign Application Priority Data

Aug. 29, 2014 (JP) ................................ 2014-175133

(51) Int. Cl.
| | |
|---|---|
| *A61K 31/51* | (2006.01) |
| *A61K 31/4415* | (2006.01) |
| *A61K 31/44* | (2006.01) |
| *A61P 13/12* | (2006.01) |
| *A61P 3/02* | (2006.01) |
| *A61P 25/32* | (2006.01) |
| *A61P 3/10* | (2006.01) |
| *A61P 19/10* | (2006.01) |
| *A61P 29/00* | (2006.01) |
| *A61P 25/18* | (2006.01) |
| *A61P 35/00* | (2006.01) |

(52) U.S. Cl.
CPC ............. *A61K 31/51* (2013.01); *A61K 31/44* (2013.01); *A61K 31/4415* (2013.01); *A61P 3/02* (2018.01); *A61P 3/10* (2018.01); *A61P 13/12* (2018.01); *A61P 19/10* (2018.01); *A61P 25/18* (2018.01); *A61P 25/32* (2018.01); *A61P 29/00* (2018.01); *A61P 35/00* (2018.01)

(58) Field of Classification Search
CPC .... A61K 31/44; A61K 31/4415; A61K 31/51; A61P 13/12; A61P 19/10; A61P 29/00; A61P 3/02; A61P 3/10; A61P 35/00; A61P 25/18; A61P 25/32
See application file for complete search history.

(56) References Cited

U.S. PATENT DOCUMENTS

| | | | |
|---|---|---|---|
| 2002/0192310 A1 | 12/2002 | Bland | |
| 2005/0272781 A1 | 12/2005 | Khalifah | |
| 2008/0161398 A1 | 7/2008 | Verlaan et al. | |
| 2011/0028470 A1 | 2/2011 | Itokawa et al. | |
| 2011/0150968 A1 | 6/2011 | Grassi | |
| 2011/0274679 A1 | 11/2011 | Pietrzkowski | |
| 2013/0338574 A1 | 12/2013 | Kakuta et al. | |
| 2014/0134222 A1 | 5/2014 | Morariu | |
| 2014/0171472 A1 | 6/2014 | Degenhardt et al. | |

FOREIGN PATENT DOCUMENTS

| | | | | |
|---|---|---|---|---|
| CN | 103458891 | | 12/2013 | |
| CN | 107148272 | | 9/2017 | |
| EP | 2476425 | A1 * | 7/2012 | ........... A23L 33/105 |
| EP | 3 187 185 | | 7/2017 | |
| JP | 11-512432 | | 10/1999 | |
| JP | 2002-527471 | | 8/2002 | |
| JP | 2009-39088 | | 2/2009 | |
| WO | 97/09981 | | 3/1997 | |
| WO | 00/23063 | | 4/2000 | |
| WO | WO-0224165 | A2 * | 3/2002 | ............. A23L 27/80 |
| WO | 2008/049615 | | 5/2008 | |
| WO | 2012/011588 | | 1/2012 | |

OTHER PUBLICATIONS

Sell et al., "Structure Elucidation of a Senescence Cross-link from Human Extracellular Matrix", The Journal of Biological Chemistry, 264(36):21597-21602 (1989).
Takeuchi, "TAGE (toxic AGEs) hypothesis in life style-related disease", Bulletin of Hokuriku University, 28:33-48 (1994), with English Abstract & Partial English Translation; cited in specification.
Nagai et al., "Significance of Advanced Glycation End Products in Aging-Related Disease", Anti-Aging Medicine, 7(10):112-119 (2010).
Nakayama et al., "Plasma α-Oxoaldehyde Levels in Diabetic and Nondiabetic Chronic Kidney Disease Patients", American Journal of Nephrology, 28(6):871-878 (2008).
Ogawa et al., "Methylglyoxal Is a Predictor in Type 2 Diabetic Patients of Intima-Media Thickening and Elevation of Blood Pressure", Hypertension, 56(3):471-476 (2010).
Sundl et al., "Antioxidant Status of Patients on Peritoneal Dialysis: Associations with Inflammation and Glycoxidative Stress", Peritoneal Dialysis International, 29(1):89-101 (2009).
Marta et al., "Advanced Glycation End-Products in Patients with Chronic Alcohol Misuse", Alcohol & Alcoholism, 39(4):316-320 (2004).

(Continued)

*Primary Examiner* — Sarah Pihonak
(74) *Attorney, Agent, or Firm* — Wenderoth, Lind & Ponack, LLP

(57) ABSTRACT

Vitamin B1 deficiency caused when a pyridoxamine compound is administered in a large amount is prevented and/or treated. A pharmaceutical composition formed by combining at least one pyridoxamine compound selected from the group consisting of pyridoxamine and pharmaceutically acceptable salts thereof and at least one thiamine compound selected from the group consisting of thiamine, derivatives thereof, and pharmaceutically acceptable salts thereof, is administered.

6 Claims, 4 Drawing Sheets

(56) References Cited

OTHER PUBLICATIONS

Junaid et al., "Proteomic Studies Identified a Single Nucleotide Polymorphism in Glyoxalase I as Autism Susceptibility Factor", American Journal of Medical Genetics Part A, 131(1):11-17 (2004).
International Search Report dated Dec. 1, 2015 in corresponding International (PCT) Application No. PCT/JP2015/073935.
Extended European Search Report dated Mar. 14, 2018 in European Application No. 15835127.0.
Engelen et al., "Current therapeutic interventions in the glycation pathway: evidence from clinical studies", Diabetes, Obesity and Metabolism, 15(8): 677-689 (2013).
Nascimento et al., "Effect of High-Dose Thiamine and Pyridoxine on Advanced Glycation End Products and Other Oxidative Stress Markers in Hemodialysis Patients: A Randomized Placebo-Controlled Study", Journal of Renal Nutrition, 16(2): 119-124 (2006).
Booth et al., "Thiamine Pyrophosphate and Pyridoxamine Inhibit the Formation of Antigenic Advanced Glycation End-Products: Comparison with Aminoguanidine" Biochemical and Biophysical Research Communications, 220(1) 113-119 (1996).
Shahmiri et al., European Journal of Nutrition, 2013, Springer-Verlag, vol. 52, pp. 1821-1824 (Year: 2013).
Ahmed et al., Diabetes Obesity and Metabolism, 2007, Blackwell Publishing Ltd. vol. 9, pp. 233-245 (Year: 2007).
Kamiyama et al., "A Clinical Study of Pyridoxine Treatment for Pervasive developmental disorders with Hypersensitivity to Sound", Official Journal of the Japanese Society of Child Neurology, vol. 38: 277-282 (2006), with partial English translation.
Hunsinger et al., "Is there abasis for novel pharmacotherapy of autism?", Life Sciences, 67: 1667-1682 (2000).
Rossignol et al., "Novel and emerging treatments for autism spectrum disorders: A systemic review", Annals of Clinical Psychiatry, 21(4): 213-236 (2009).
Khahn et al., "The role of thiamine in autism", American Journal of Psychiatry and Neuroscience, 1(2): 22-37 (2013).
Diagnostic and Statistical Manual of Mental Disorders Fifth Edition, Feb. 15, 2015, vol. 1, pp. 31-32, 49-57.
"Pyridoxine treatment in a subgroup of children with pervasive developmental disorders", Developmental Medicine and Child Neurology, 44(4): 283-286 (2002).
Nye et al., "Combined vitamin B6-magnesium treatment in autism spectrum disorder (Review)", Cochrane Database of Systematic Reviews, issue 4, Art. CD003497. DOI10.1002/14651858.CD003497. pub2.
Grant-in-Aid for Scientific Research (KAKENHI) Research Result Report, May 2010, with English Abstract.
Baxter et al., "Pyridoxine-dependent Seizures: Demographic, Clinical, MRI and Psychometric Features, and Effect of Dose on Intelligence Quotient", Developmental Medicine and Child Neurology, vol. 38: 998-1006 (1996).
Lofthouse et al., "A review of Complementary and Alternative Treatments for Autism Spectrum Disorders" Autism Research and Treatment, Article ID 870391, 1-21 (2012).
Rimland, "An Orthomolecular Study of Psychotic Children", Orthomolecular Psychiatry, 3(4): 371-377 (1974).
Merck Manual, 18th Edition, Japanese Version, 2007, pp. 39-40, with Partial English translation.
Office Action, dated Aug. 16, 2016, issued in Japanese Patent Application No. 2016-040492, with English translation.
International SearchReport, dated May 9, 2017 in International (PCT) Application No. PCT/JP2017/008355.
Hamada, "Nerve tissue damage caused by thiamine (vitamin B1) deficiency", Comp. Physiol. Biochem. 31(1):13-19, 2014, partial English translation.
Supplementary European Search Report dated Oct. 1, 2019 in European Application No. 17760149.9.
Hagiwara et al., Met. Clin. & Exp., 2009, Elsevier, vol. 58, pp. 934-945 (Year: 2009).
Office Action dated Jan. 24, 2020 in European Patent Application No. 15 835 127.0.
Office Action dated Apr. 14, 2020 in corresponding Chinese Patent Application No. 201580059256.2, with English translation.
Schopler, Eric et al., "Medical Treatment of Autistic People", in *Neurobiological Issues in Autism*, in, Plenum Press, New York, 1987, p. 381.
Arai, Makoto et al., "Schizophrenia and Carbonyl Stress", *Journal of Nerve*, 2012, vol. 114, pp. 101-106, with English Abstract.
Office Action dated Apr. 28, 2020 in corresponding Chinese Patent Application No. 201780015030.1, with English translation.

* cited by examiner

FIG. 2

| Patient ID | Period | 0w | 1w | 2w | 3w | 4w | 5w | 6w | 7w | 8w | 9w | 10w | 11w | 12w | 13w | 14w | 15w | 16w | 17w | 18w | 19w | 20w | 21w | 22w | 23w | 24w |
|---|---|---|---|---|---|---|---|---|---|---|---|---|---|---|---|---|---|---|---|---|---|---|---|---|---|---|
| 3 | Wernicke's encephalopathy | | | | | | | ★ | | | | | | | | ● | | | | | | | | | | |
| 3 | PM dose (mg/one time) | 400 | 400 | 600 | 600 | 600 | 600 | 400 | 400 | 400 | 400 | 400 | 400 | 400 | 400 | 400 | 400 | 400 | 400 | 400 | 400 | 400 | 400 | 400 | 400 | 400 |
| 3 | VB1 dose (mg/day daily) | | | | | | | 75 | 75 | 75 | 75 | 75 | 75 | 75 | 75 | 75 | 75 | 75 | 75 | 75 | 75 | 75 | 75 | 75 | 75 | 75 |
| 3 | Whole blood VB1 amount (ng/mL) | | | | | | | 28 | | 82.3 | | | | 135 | | | | 138 | | | | 127 | | | | |
| 3 | Serum PM concentration (ng/mL) | 0.2 | | 1462 | | | | | | | | | | 23.2 | | | | 218 | | | | | | | | 75 |
| 3 | Serum PL concentration (ng/mL) | 6.2 | | 1951 | | 1991 | | | | 1414 | | | | 1179 | | | | 2268 | | | | 1785 | | | | 1903 |
| 3 | Serum PN concentration (ng/mL) | 3 | | 90 | | 162 | | | | 5.6 | | | | 3 | | | | 15.3 | | | | 8 | | | | 4.8 |
| 6 | Wernicke's encephalopathy | | | | | | | | | | ★ | | ● | | | | | | | | | | | | | |
| 6 | PM dose (mg/one time) | 400 | 600 | 600 | 400 | 400 | 400 | 400 | 400 | 600 | 400 | 400 | 400 | 400 | 400 | 400 | 400 | 400 | 400 | | | | | | | |
| 6 | VB1 dose (mg/day daily) | | | | | | | | | | 300 | 100 | 100 | 100 | 50 | 50 | 50 | 50 | 50 | | | | | | | |
| 6 | Whole blood VB1 amount (ng/mL) | | | | | | | | | | 25 | | 150 | 117 | 113 | | | | | | | | | | | |
| 6 | Serum PM concentration (ng/mL) | 0.2 | | 1526 | | 320 | | | | 421 | | | | 140 | | | | 107 | | | | | | | | |
| 6 | Serum PL concentration (ng/mL) | 3.5 | | 3594 | | | | | | 2968 | | | | 3941 | | | | 2527 | | | | | | | | |
| 6 | Serum PN concentration (ng/mL) | 3 | | 162 | | | | | | 28.6 | | | | 8 | | | | 7.7 | | | | | | | | |

Star symbols: Onset of Wernicke's encephalopathy, Solid circles: Disappearance of Wernicke's encephalopathy
PM: pyridoxamine, PL: pyridoxal, PN: pyridoxine, VB1: vitamin B1
Pyridoxamine was administered at the above dose three times a day.

PHARMACEUTICAL COMPOSITION FORMED BY COMBINING PYRIDOXAMINE COMPOUND AND THIAMINE COMPOUND

TECHNICAL FIELD

The present invention relates to a pharmaceutical composition formed by combining a pyridoxamine compound and a thiamine compound. The present invention also relates to a pharmaceutical composition or a pharmaceutical product used in combination with a thiamine compound at use. The present invention also relates to a method for preventing and/or treating vitamin B1 deficiency caused by administration of a pyridoxamine compound.

BACKGROUND ART

Advanced glycation end products ("AGEs") are substances formed in the body by a non-enzymatic reaction between an amino group of a protein and a carbonyl compound produced from sugar, lipid, etc., under conditions of hyperglycemia and oxidative stress (Maillard reaction). AGEs are a heterogeneous group of many substances. Pentosidine, which is one type of AGE structure, is a fluorescent substance that was isolated from human dura mater collagen by Sell et al. in 1989 (NPL 1).

A factor for causing accumulation of AGEs is, for example, carbonyl stress. Carbonyl stress is a state in which carbonyl modification of proteins is increased by reactive carbonyl compounds ("RCOs") in the body. For example, in diabetes, due to hyperglycemia, an increase in the levels of sugar-derived carbonyl compounds and carbonyl-modified proteins (AGEs) is observed (NPL 2 and 3). Due to the decreased excretion of carbonyl compounds and increased oxidative stress in renal failure, and the increased oxidative stress in inflammatory diseases, the production of carbonyl compounds is enhanced, and thus an increase in the level of carbonyl-modified proteins (AGEs) is observed (NPL 3, 4, 5, and 6). Further, it has been reported that AGE levels also increase in patients who are deficient in glyoxalase, which is an enzyme for removing carbonyl compounds (PTL 1). It has also been revealed that AGE levels increase in tissues and blood in various pathological conditions, such as atherosclerosis (NPL 3), diabetic retinopathy, cataracts, macular degeneration, and like age-related diseases (NPL 3), alcoholism (NPL 7), autism (NPL 8), and schizophrenia (PTL 1).

In these diseases, the AGEs in blood are not only present in high amounts, but also involved in the onset and progress of the pathological conditions. For example, it has been reported that in diabetic nephropathy, macular degeneration, etc., AGEs stimulate the cell surface receptor RAGE, resulting in occurrence and progress of the pathological conditions (NPL 3).

Thus, prevention of the onset and progress of serious diseases (pathological conditions) in which AGEs are involved, and treatment for such diseases, are attempted by administering a carbonyl scavenger, such as pyridoxamine or an edaravone analogue, to suppress accumulation of AGEs (NPL 3 and PTL 1).

CITATION LIST

Patent Literature

PTL 1: JP2009-039088A

Non-Patent Literature

NPL 1: Sell DR and Monnier V M, J Biol Chem, 1989, 264(36), pp. 21597-21602.
NPL 2: Takeuchi Masayoshi, Bulletin of Hokuriku University, 1994, No. 28, pp. 33-48.
NPL 3: Nagai Ryoji et al., Anti-Aging Medicine, 2010, 7(10), pp. 112-119.
NPL 4: Nakayama K et al., Am J Nephrol, 2008, 28(6), pp. 871-878.
NPL 5: Ogawa S et al., Hypertension, 2010, 56(3), pp. 471-476.
NPL 6: Sundl I et al., Perit Dial Int, 2009, 29(1), pp. 89-101.
NPL 7: Kalousova M et al., Alcohol Alcohol, 2004, 39(4), pp. 316-320.
NPL 8: Junaid M A, et al., Am J Med Genet A, 2004, 131(1), pp. 11-17.

SUMMARY OF INVENTION

Technical Problem

As described above, administration of a carbonyl scavenger to subjects, in particular, patients in which an increase or accumulation of AGEs is observed has been considered to suppress the production and accumulation of AGEs.

However, the research of the present inventor found that the amount of vitamin B1 in the body is decreased by administering pyridoxamine in a relatively large amount.

Not less than 80% of vitamin B1 is present in the body as thiamine diphosphate, which is an activated form. Thiamine diphosphate mediates decarboxylation of pyruvic acid as a coenzyme of pyruvate decarboxylase and helps the production of acetyl-CoA, which is essential for the initiation of the citric acid cycle. Thiamine diphosphate also acts as a coenzyme of dehydrogenase, which catalyzes oxidative decarboxylation of $\alpha$-keto acids, and transketolase, which catalyzes keto group transfer, and thiamine diphosphate helps $\alpha$-oxidation.

As described above, since vitamin B1 is deeply involved in energy metabolism in the body, deficiency in vitamin B1 causes various symptoms (vitamin B1 deficiency), such as beriberi, axial optic neuritis, polyneuritis, Wernicke's encephalopathy, Korsakoff's syndrome, decreased appetite, and/or digestion disorders.

An object of the present invention is to prevent and/or treat vitamin B1 deficiency believed to be caused by administering a carbonyl scavenger, in particular, a pyridoxamine compound in a specific amount or more. Another object of the present invention is to provide a pharmaceutical composition for preventing and/or treating vitamin B1 deficiency that can be caused by administering a carbonyl scavenger, in particular, a pyridoxamine compound in a specific amount or more.

Solution to Problem

The present invention has been accomplished based on the finding that administration of a relatively large amount of a pyridoxamine compound to a patient with a disease or symptom in which AGES are involved decreases the amount of vitamin B1 in the body, causing vitamin B1 deficiency, and that the vitamin B1 deficiency can be prevented and treated by administering a pyridoxamine compound in combination with a thiamine compound.

The present invention provides the following.

(I) Combination Pharmaceutical Composition (I-1) A pharmaceutical composition formed by combining
(1) at least one pyridoxamine compound selected from the group consisting of pyridoxamine and pharmaceutically acceptable salts thereof, and
(2) at least one thiamine compound selected from the group consisting of thiamine, derivatives thereof, and pharmaceutically acceptable salts thereof,
the daily dose of (1) the pyridoxamine compound being 300 mg or more calculated as pyridoxamine.

(I-2) The pharmaceutical composition according to (I-1), wherein the daily dose of (2) the thiamine compound is 1 to 20 parts by weight per 100 parts by weight of the daily dose of (1) the pyridoxamine compound.

(I-3) The pharmaceutical composition according to (I-1) or (I-2), wherein the pharmaceutical composition is administered to a subject having at least one disease or symptom selected from the group consisting of diabetes, diabetic complications, chronic renal failure, complications of chronic renal failure, nephropathy, nephritis, inflammatory diseases, atherosclerosis, age-related eye diseases, neurodegenerative diseases (including Alzheimer-type dementia; the same applies hereinafter), alcoholism, autism, schizophrenia, malignant melanoma, osteoporosis, deterioration of the peritoneum in peritoneal dialysis, chronic rheumatism, and atopic dermatitis.

(I-4) The pharmaceutical composition according to any one of (I-1) to (I-3), wherein the pharmaceutical composition is administered to a subject having at least one disease or symptom selected from the group consisting of beriberi, axial optic neuritis, polyneuritis, Wernicke's encephalopathy, decreased appetite, and digestion disorders.

(I-5) The pharmaceutical composition according to any one of (I-1) to (I-4), wherein the pharmaceutical composition is a pharmaceutical composition for the treatment of an advanced glycation end product-related disease and the prevention and/or treatment of vitamin B1 deficiency.

(I-6) The pharmaceutical composition according to (I-5), wherein the vitamin B1 deficiency is caused by administration of a pyridoxamine compound.

(I-7) The pharmaceutical composition according to (I-5) or (I-6), wherein the advanced glycation end product-related disease is at least one disease selected from the group consisting of diabetes, diabetic complications, chronic renal failure, complications of chronic renal failure, nephropathy, nephritis, inflammatory diseases, atherosclerosis, age-related eye diseases, neurodegenerative diseases, alcoholism, autism, schizophrenia, malignant melanoma, osteoporosis, deterioration of the peritoneum in peritoneal dialysis, chronic rheumatism, and atopic dermatitis.

(I-8) The pharmaceutical composition according to any one of (I-1) to (I-7), wherein (1) the pyridoxamine compound and (2) the thiamine compound are individually packaged alone or with a pharmaceutically acceptable carrier or additive, as separate preparations, and wherein the pyridoxamine compound or a preparation containing the pyridoxamine compound, and the thiamine compound or a preparation containing the thiamine compound, are administered to a subject at different times, at the same time, or in parallel.

(I-9) The pharmaceutical composition according to (I-8), wherein the pyridoxamine compound or the preparation containing the pyridoxamine compound is administered to the subject before the start of administration of the thiamine compound or the preparation containing the thiamine compound, or the pyridoxamine compound or the preparation containing the pyridoxamine compound is administered to the subject after the start of administration of the thiamine compound or the preparation containing the thiamine compound.

(I-10) The pharmaceutical composition according to any one of (I-1) to (I-9), wherein the pyridoxamine compound or the preparation containing the pyridoxamine compound, and/or the thiamine compound or the preparation containing the thiamine compound, is in a dosage form for administration selected from the group consisting of oral administration, intramuscular injection, subcutaneous injection, and intravascular administration.

(I-11) The pharmaceutical composition according to any one of (I-1) to (I-7), wherein the pharmaceutical composition is a combination drug in which (1) the pyridoxamine compound and (2) the thiamine compound are contained in the same preparation.

(I-12) The pharmaceutical composition according to (I-11), wherein the combination drug is in a dosage form for administration selected from the group consisting of oral administration, intramuscular injection, subcutaneous injection, and intravascular administration.

(I-13) The pharmaceutical composition according to any one of (I-1) to (I-12), wherein the pharmaceutical composition is administered to a subject having a serum or plasma concentration of at least one compound selected from the group consisting of pentosidine, carboxymethyllysine, and 3-deoxyglucosone at the following level:
(a) pentosidine: 45 ng/ml or more
(b) carboxymethyllysine: 6.5 µg/ml or more
(c) 3-deoxyglucosone: 20 ng/ml or more.

(I-14) The pharmaceutical composition according to any one of (I-1) to (I-13), wherein the pharmaceutical composition is administered to a subject in which the whole blood vitamin B1 concentration is 30 ng/ml or less.

(I-15) Compounds for use in the treatment of an advanced glycation end product-related disease and the prevention and/or treatment of vitamin B1 deficiency, the compounds being the following (1) and (2):
(1) at least one pyridoxamine compound selected from the group consisting of pyridoxamine and pharmaceutically acceptable salts thereof (provided that the daily dose of the pyridoxamine compound is 300 mg or more calculated as pyridoxamine), and
(2) at least one thiamine compound selected from the group consisting of thiamine, derivatives thereof, and pharmaceutically acceptable salts thereof.

(I-16) Use of the pharmaceutical composition according to any one of (I-1) to (I-14) for the production of a pharmaceutical composition for the treatment of an advanced glycation end product-related disease and the prevention and/or treatment of vitamin B1 deficiency.

(II) Pharmaceutical Product Used in Combination with Thiamine Compound (II-1) A pharmaceutical product comprising:
(A) a packaged pharmaceutical composition containing at least one pyridoxamine compound selected from the group consisting of pyridoxamine and pharmaceutically acceptable salts thereof as an active ingredient; and
(B) at least one document selected from the group consisting of a package insert, a product label, directions, and instructions, each stating that the pharmaceutical composition is used in combination with at least one thiamine compound selected from the group consisting of thiamine, derivatives thereof, and pharmaceutically acceptable salts thereof, for the treatment of an advanced glycation end product-related disease.

(II-2) The pharmaceutical product according to (II-1), wherein the daily dose of the pyridoxamine compound in (A) the packaged pharmaceutical composition is 300 mg or more calculated as pyridoxamine, and the daily dose is stated in (B).

(II-3) The pharmaceutical product according to (II-1) or (II-2), wherein the advanced glycation end product-related disease is at least one disease selected from the group consisting of diabetes, diabetic complications, chronic renal failure, complications of chronic renal failure, nephropathy, nephritis, inflammatory diseases, atherosclerosis, age-related eye diseases, neurodegenerative diseases, alcoholism, autism, schizophrenia, malignant melanoma, osteoporosis, deterioration of the peritoneum in peritoneal dialysis, chronic rheumatism, and atopic dermatitis.

(II-4) The pharmaceutical product according to any one of (II-1) to (II-3), for use in administration to a subject having at least one disease or symptom selected from the group consisting of beriberi, axial optic neuritis, polyneuritis, Wernicke's encephalopathy, decreased appetite, and digestion disorders.

(II-5) The pharmaceutical product according to any one of (II-1) to (II-4), wherein (A) the packaged pharmaceutical composition is administered to a subject having a serum or plasma concentration of at least one compound selected from the group consisting of pentosidine, carboxymethyllysine, and 3-deoxyglucosone at the following level:
(a) pentosidine: 45 ng/ml or more
(b) carboxymethyllysine: 6.5 μg/ml or more
(c) 3-deoxyglucosone: 20 ng/ml or more.

(II-6) The pharmaceutical product according to any one of (II-1) to (II-5), for use in administration to a subject in which the whole blood vitamin B1 concentration is 30 ng/ml or less.

(II-7) The pharmaceutical product according to any one of (II-1) to (II-6), wherein the pharmaceutical product is a drug for treating an advanced glycation end product-related disease.

(III) Pharmaceutical Composition Used in Combination with Thiamine Compound (III-1) A pharmaceutical composition comprising at least one pyridoxamine compound selected from the group consisting of pyridoxamine and pharmaceutically acceptable salts thereof as an active ingredient, the pharmaceutical composition being used in combination with at least one thiamine compound selected from the group consisting of thiamine, derivatives thereof, and pharmaceutically acceptable salts thereof, for the treatment of an advanced glycation end product-related disease at a daily dose of 300 mg or more calculated as pyridoxamine.

(III-2) The pharmaceutical composition according to (III-1), wherein the advanced glycation end product-related disease is at least one disease selected from the group consisting of diabetes, diabetic complications, chronic renal failure, complications of chronic renal failure, nephropathy, nephritis, inflammatory diseases, atherosclerosis, age-related eye diseases, neurodegenerative diseases, alcoholism, autism, schizophrenia, malignant melanoma, osteoporosis, deterioration of the peritoneum in peritoneal dialysis, chronic rheumatism, and atopic dermatitis.

(III-3) The pharmaceutical composition according to (III-1) or (III-2), wherein the pharmaceutical composition is administered to a subject having at least one disease or symptom selected from the group consisting of beriberi, axial optic neuritis, polyneuritis, Wernicke's encephalopathy, decreased appetite, and digestion disorders.

(III-4) The pharmaceutical composition according to any one of (III-1) to (III-3), wherein the pharmaceutical composition is administered to a subject having a serum or plasma concentration of at least one compound selected from the group consisting of pentosidine, carboxymethyllysine, and 3-deoxyglucosone at the following level:
(a) pentosidine: 45 ng/ml or more
(b) carboxymethyllysine: 6.5 μg/ml or more
(c) 3-deoxyglucosone: 20 ng/ml or more.

(III-5) The pharmaceutical composition according to any one of (III-1) to (III-4), wherein the pharmaceutical composition is administered to a subject in which the whole blood vitamin B1 concentration is 30 ng/ml or less.

(III-6) The pharmaceutical composition according to any one of (III-1) to (III-5), wherein the pharmaceutical composition is a drug for treating an advanced glycation end product-related disease.

(IV) Method for Preventing and/or Treating Advanced Glycation End Product-Related Disease (IV-1) A method for preventing and/or treating an advanced glycation end product-related disease, the method comprising administering
(1) at least one pyridoxamine compound selected from the group consisting of pyridoxamine and pharmaceutically acceptable salts thereof and
(2) at least one thiamine compound selected from the group consisting of thiamine, derivatives thereof, and pharmaceutically acceptable salts thereof, to a subject simultaneously or separately, the daily dose of the pyridoxamine compound being 300 mg or more calculated as pyridoxamine.

(IV-2) The method according to (IV-1), wherein the advanced glycation end product-related disease is at least one disease selected from the group consisting of diabetes, diabetic complications, chronic renal failure, complications of chronic renal failure, nephropathy, nephritis, inflammatory diseases, atherosclerosis, age-related eye diseases, neurodegenerative diseases, alcoholism, autism, schizophrenia, malignant melanoma, deterioration of the peritoneum in peritoneal dialysis, chronic rheumatism, and atopic dermatitis.

(IV-3) The method according to (IV-1) or (IV-2), wherein the subject has at least one disease or symptom selected from the group consisting of beriberi, axial optic neuritis, polyneuritis, Wernicke's encephalopathy, decreased appetite, and digestion disorders.

(IV-4) The method according to any one of (IV-1) to (IV-3), wherein the subject has a serum or plasma concentration of at least one compound selected from the group consisting of pentosidine, carboxymethyllysine, and 3-deoxyglucosone at the following level:
(a) pentosidine: 45 ng/ml or more
(b) carboxymethyllysine: 6.5 μg/ml or more
(c) 3-deoxyglucosone: 20 ng/ml or more.

(IV-5) The method according to any one of (IV-1) to (IV-4), wherein the whole blood vitamin B1 concentration in the subject is 30 ng/ml or less.

(V) Method for Preventing and/or Treating Vitamin B1 Deficiency Caused by Administration of Pyridoxamine Compound (V-1) A method for preventing and/or treating vitamin B1 deficiency caused by administration of a pyridoxamine compound, the method comprising administering
(1) at least one pyridoxamine compound selected from the group consisting of pyridoxamine and pharmaceutically acceptable salts thereof and (2) at least one thiamine compound selected from the group consisting of thiamine, derivatives thereof, and pharmaceutically acceptable salts thereof,
to a subject simultaneously or separately,
the serum or plasma concentration of at least one compound selected from the group consisting of pentosidine, carboxymethyllysine, and 3-deoxyglucosone in the subject before administration of the pyridoxamine compound being as follows:
(a) pentosidine: 45 ng/ml or more
(b) carboxymethyllysine: 6.5 μg/ml or more
(c) 3-deoxyglucosone: 20 ng/ml or more.
(V-2) The method according to (V-1), wherein the vitamin B1 deficiency is caused by administration of a pyridoxamine compound.

Advantageous Effects of Invention

With the present invention, vitamin B1 deficiency that can be caused by administering a pyridoxamine compound in a specific amount or more, specifically, not less than 300 mg/day, can be prevented and/or treated. In particular, the present invention makes it possible to prevent or improve symptoms and pathological conditions due to the production and accumulation of AGEs by administering a pyridoxamine compound to suppress the production and accumulation of AGEs, and enables prevention and/or treatment of vitamin B1 deficiency showing at least one symptom selected from the group consisting of beriberi, axial optic neuritis, polyneuritis, Wernicke's encephalopathy, decreased appetite, digestion disorders, and the like, which can be caused by administering the pyridoxamine compound in the above amount or more.

BRIEF DESCRIPTION OF DRAWINGS

FIG. 2 shows protocols of administration of a pyridoxamine compound (pyridoxamine dihydrochloride: referred to as "PM" in FIG. 2) and a thiamine compound (fursultiamine: referred to as "VB1" in FIG. 2) to two schizophrenia patients (ID: Nos. 3 and 6), and shows the whole blood vitamin B1 (VB1) amount, serum pyridoxamine (PM) concentration, pyridoxal (PL) concentration, and pyridoxine (PN) concentration in these patients measured over time. The star symbols indicate points in time at which Wernicke's encephalopathy was suspected, and the solid circles indicate points in time at which Wernicke's encephalopathy disappeared.

DESCRIPTION OF EMBODIMENTS

1. Combination Pharmaceutical Composition

Figure 1:
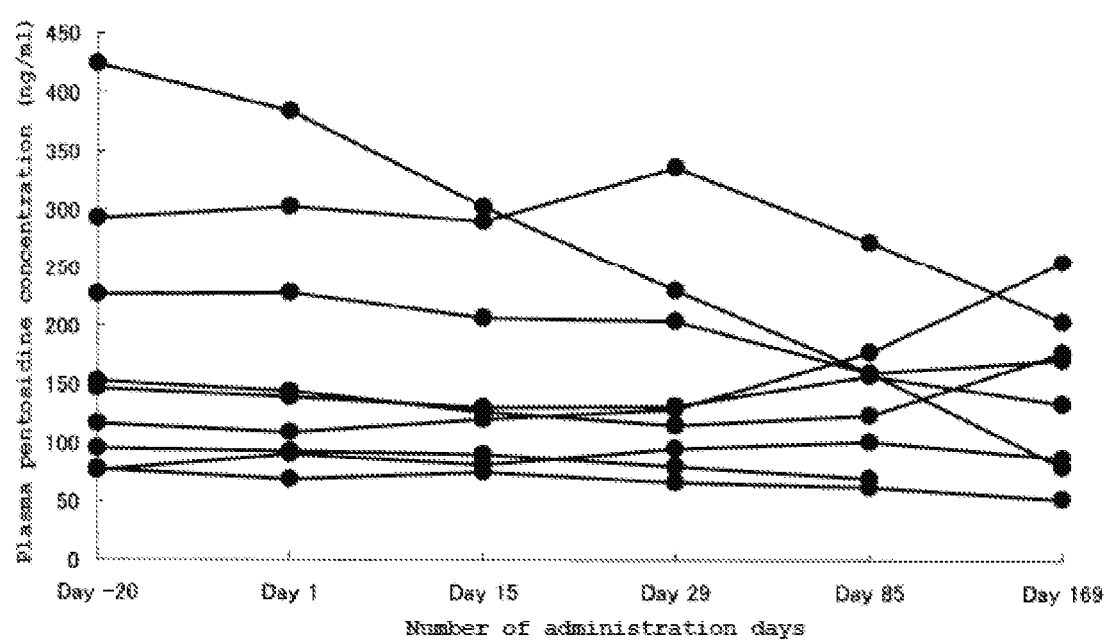
FIG. 1 shows results of evaluating the effect of administering a pyridoxamine compound on schizophrenia patients by monitoring the plasma pentosidine concentration (Reference Experiment Example). The vertical axis indicates the plasma pentosidine concentration (ng/ml), and the horizontal axis indicates the number of days of administration of a pyridoxamine compound.

The pharmaceutical composition of the present invention is formed by combining (1) at least one pyridoxamine compound selected from the group consisting of pyridoxamine and pharmaceutically acceptable salts thereof and (2) at least one thiamine compound selected from the group consisting of thiamine, derivatives thereof, and pharmaceutically acceptable salts thereof.

The term "pyridoxamine compound" as used herein refers to at least one member selected from the group consisting of pyridoxamine (IUPAC name: 4-(aminomethyl)-5-(hydroxymethyl)-2-methylpyridin-3-ol) and pharmaceutically acceptable salts thereof. These can be used singly or in a combination of two or more.

Examples of pharmaceutically acceptable salts include, but are not particularly limited to, acid addition salts with inorganic acids, such as hydrochloric acid, hydrobromic acid, hydroiodic acid, sulfuric acid, nitric acid, and phosphoric acid, or organic acids, such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid, and glutamic acid; inorganic salts of sodium, potassium (which are alkali metal salts), magnesium, calcium (which are alkaline earth metal salts), aluminum, and the like; salts with organic bases, such as methylamine, ethylamine, ethanolamine, lysine, and ornithine; ammonium salts; and the like. Acid addition salts with hydrochloric acid; and inorganic salts of sodium, potassium, magnesium, calcium, aluminum, and the like are preferable; and pyridoxamine dihydrochloride is most preferable.

As shown below, when absorbed in the body, pyridoxamine compounds are phosphorylated due to the activity of a kinase, thereby being converted into pyridoxamine 5'-phosphate (PMP). PMP is further converted into pyridoxal 5'-phosphate (PLP) due to the activity of an oxidase. This PLP is an activated form of pyridoxamine compounds in the body. Further, PLP is dephosphorylated due to the activity of a phosphatase, thereby being converted into pyridoxal (PL). PL is further metabolized to 4-pyridoxic acid (4-PA) due to the activity of an oxidase.

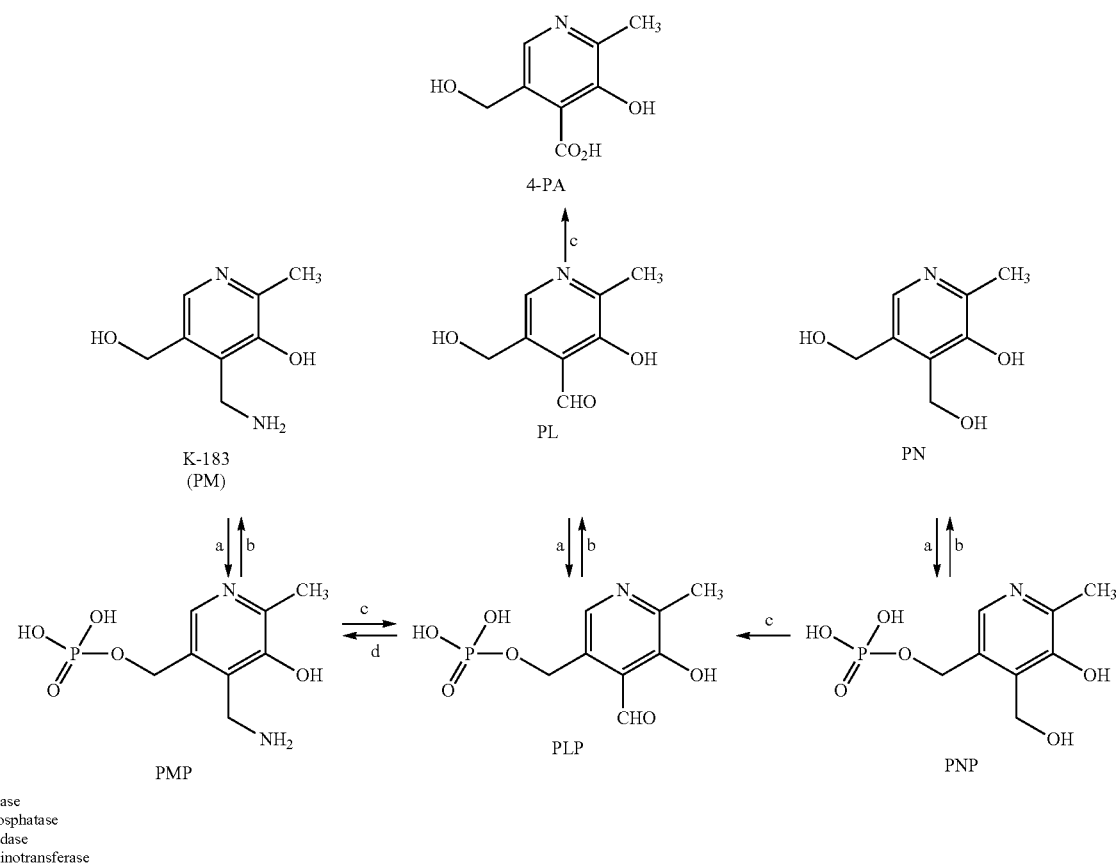

Metabolic pathway of pyridoxamine (PM)

a: kinase
b: phosphatase
c: oxidase
d: aminotransferase

The term "thiamine compound" as used herein refers to at least one member selected from the group consisting of thiamine, derivatives thereof, and pharmaceutically acceptable salts thereof. Thus, these can be used singly or in a combination of two or more.

The thiamine derivatives may be in disulfide form, acyl form, or mixtures thereof. Examples of thiamine derivatives include bisthiamine, thiamine disulfide, thiamine dicetyl sulfuric acid ester salts, benfotiamine, prosultiamine, fursultiamine, bisbentiamine, cycotiamine, octotiamine, allithiamine, prosultiamine, thiamine tetrahydrofurfuryl disulfide, dicethiamine, bisbuthiamine, bisibuthiamine, thiamine monophosphate disulfide, thiamine pyrophosphate, cycotiamine, thiamine ethyl disulfide, and the like. The thiamine derivative is preferably at least one member selected from the group consisting of octotiamine, prosultiamine, fursultiamine, bisbentiamine, benfotiamine, cocarboxylase, and thiamine disulfide, more preferably at least one member selected from the group consisting of octotiamine, prosultiamine, and fursultiamine, and even more preferably fursultiamine.

Examples of pharmaceutically acceptable salts of thiamine and derivatives thereof include, but are not particularly limited to, acid addition salts with inorganic acids, such as hydrochloric acid, hydrobromic acid, hydroiodic acid, sulfuric acid, nitric acid, and phosphoric acid, or organic acids, such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid, and glutamic acid; inorganic salts of sodium, potassium (which are alkali metal salts), magnesium, calcium (which are alkaline earth metal salts), aluminum, and the like; salts with organic bases, such as methylamine, ethylamine, ethanolamine, lysine, and ornithine; ammonium salts; and the like. Acid addition salts with hydrochloric acid; inorganic salts of sodium, potassium, magnesium, calcium, aluminum, and the like are preferable; and acid addition salts with inorganic acids, such as hydrochloride and nitrate, are most preferable.

The thiamine compound is preferably at least one member selected from the group consisting of octotiamine, prosultiamine, fursultiamine, bisbentiamine, benfotiamine, cocarboxylase, thiamine disulfide, and salts thereof; thiamine chloride hydrochloride; thiamine nitrate; and dicethiamine hydrochloride, more preferably at least one member selected from the group consisting of octotiamine, prosultiamine, fursultiamine, and salts thereof, and even more preferably fursultiamine or salts thereof (e.g., fursultiamine hydrochloride).

The phrase "formed by combining" as used herein is used with meaning including the following cases for the pharmaceutical composition of the present invention:
(i) the pyridoxamine compound and the thiamine compound are contained in the form of a mixture in the same preparation (combination drug),
(ii) the pyridoxamine compound alone or a preparation containing the pyridoxamine compound, and the thiamine compound alone or a preparation containing the thiamine compound, are individually packaged as separate preparations and sold as a combination (a kit),
(iii) the pyridoxamine compound alone or a preparation containing the pyridoxamine compound, and the thiamine compound alone or a preparation containing the thiamine compound, are separate preparations, and these are sold in combination as a package, or
(iv) the pyridoxamine compound alone or a preparation containing the pyridoxamine compound, and the thiamine compound alone or a preparation containing the thiamine compound, are individually packaged as separate preparations, marketed through separate distribution channels, and used in combination at use.

More specifically, the "pharmaceutical composition formed by combining" of the present invention may be used in such a manner that the pyridoxamine compound or a preparation containing the pyridoxamine compound, and the thiamine compound or a preparation containing the thiamine compound are administered to a subject at different times, at the same time, or in parallel, regardless of what forms the pyridoxamine compound and the thiamine compound take during the distribution stage, including sale. The above usage includes a usage in which the pyridoxamine compound or a preparation containing the pyridoxamine compound is administered to a subject before the start of administration of the thiamine compound or a preparation containing the thiamine compound, and a usage in which the pyridoxamine compound or a preparation containing the pyridoxamine compound is administered to a subject after the start of administration of the thiamine compound or a preparation containing the thiamine compound.

The phrase "preparation containing the pyridoxamine compound" here refers to a preparation containing the pyridoxamine compound in combination with one or more other components, and the phrase "preparation containing the thiamine compound" here refers to a preparation containing the thiamine compound in combination with one or more other components. The preparation containing the pyridoxamine compound and the preparation containing the thiamine compound are respectively distinguished from a preparation consisting of the pyridoxamine compound alone and a preparation consisting of the thiamine compound alone. Examples of other components include the carriers and additives for preparations described below.

The daily dose of the pyridoxamine compound is 300 mg or more calculated as pyridoxamine. The minimum daily dose of the pyridoxamine compound is 300, 400, 500, 600, 700, or 800 mg calculated as pyridoxamine, from which a more preferable minimum dose can be suitably selected. When the minimum daily dose (mg/day) is converted into the amount per kg of body weight, assuming that the body weight is 60 kg, the minimum daily dose is 5, 6.7, 8.3, 10, or 13.3 mg/kg calculated as pyridoxamine. The maximum daily dose is 2,000, 3,000, 4,000, 5,000, or 10,000 mg calculated as pyridoxamine, from which a more preferable maximum dose can be suitably selected. In terms of the amount per kg of body weight, assuming that the body weight is 60 kg, the maximum daily dose is 33.3, 50.0, 66.7, 83.3, or 166.7 mg/kg calculated as pyridoxamine.

When the daily dose of the pyridoxamine compound is 300 mg or more calculated as pyridoxamine as described above, the vitamin B1 concentration in the body decreases, and thus vitamin B1 deficiency, which is a side effect, is likely to occur. This is especially pronounced in low-weight subjects, such as elderly people and children. Even if the subject is not of low weight, the side effect tends to occur as the daily dose of the pyridoxamine compound increases, i.e., in increasing order of 300 mg or more, 400 mg or more, 500 mg or more, 600 mg or more, 700 mg or more, and 800 mg or more.

The pyridoxamine compound may be administered once a day at the dose described above. If necessary, the daily dose may be administered in two, three, four, or five portions a day, and preferably two or three portions a day.

The pyridoxamine compound can be administered for a length of time necessary for the prevention or treatment of a disease. The administration period is, for example, 1, 4, 10, 20, 30, or 50 weeks or more, from which a more preferable administration period can be suitably selected. The pyridoxamine compound can be administered daily, every other day, or every three days, and preferably daily. A roughly one-day cessation may be taken every 5 to 7 days.

The daily dose of the thiamine compound is not particularly limited, and the content of thiamine in a distributed vitamin preparation can be applied. For example, the minimum daily dose of the thiamine compound is 1, 2, 5, or 10 mg or more calculated as thiamine per day, from which a more preferable minimum dose can be suitably selected. The maximum daily dose is 50, 100, 300, or 500 mg calculated as thiamine, from which a more preferable maximum dose can be suitably selected.

The daily dose of the thiamine compound is 1 to 20 parts by weight per 100 parts by weight of the daily dose of the pyridoxamine compound. The lower limit is preferably 1, 1.5, or 3 parts by weight. The upper limit is preferably 10, 15, or 20 parts by weight.

The thiamine compound may be administered once a day at the dose described above. If necessary, the daily dose may be administered in two, three, four, or five portions a day, and preferably two or three portions a day.

The administration period for the thiamine compound is 10 to 50 weeks, and more preferably 20 to 30 weeks; however, the administration of the thiamine compound may be ended at the same time as the end of administration of the pyridoxamine compound. The thiamine compound can be administered daily, every other day, or every three days, and preferably daily. A roughly one-day cessation may be taken every 5 to 7 days. The thiamine compound may be administered in the same manner as administration of the pyridoxamine compound.

The pyridoxamine compound and the thiamine compound can be individually administered alone or as preparations containing one or more other components in combination with them (a preparation containing the pyridoxamine compound and a preparation containing the thiamine compound) by, for example, oral administration, intramuscular injection, subcutaneous injection, and/or intravascular administration.

The preparation containing the pyridoxamine compound and/or the thiamine compound can be prepared by using the pyridoxamine compound and/or the thiamine compound in combination with one or more suitable carriers or additives for preparations. Carriers and additives that can be used when the preparation is prepared are selected according to the dosage form of the preparation. Examples include those that are widely used in typical drugs, such as excipients, binders, disintegrators, lubricants, coloring agents, taste enhancers, flavor enhancers, surfactants, and the like.

The dosage form of the preparation for oral administration is not particularly limited, and examples include tablets, powders, granules, capsules (including hard capsules and soft capsules), fluids, pills, suspensions, emulsions, and the like. The dosage form of the preparation for parenteral administration include injections, drops, suppositories, nasal drops, preparations for transpulmonary administration, and the like.

When the preparation is prepared in the form of solid oral preparations, such as tablets, powders, granules, pills, and capsules, examples of usable carriers include the following: excipients such as lactose, saccharose, sodium chloride, glucose, urea, starch, calcium carbonate, kaolin, crystalline cellulose, silicic acid, methylcellulose, glycerol, sodium alginate, and gum arabic; binders such as simple syrups, liquid glucose, liquid starch, gelatin solutions, polyvinyl alcohol, polyvinyl ether, polyvinylpyrrolidone, carboxymethylcellulose, shellac, methylcellulose, ethylcellulose, water, ethanol, and potassium phosphate; disintegrators such as dried starch, sodium alginate, powdered agar, powdered laminaran, sodium hydrogencarbonate, calcium carbonate, polyoxyethylene sorbitan fatty acid esters, sodium lauryl sulfate, stearic acid monoglycerides, starch, and lactose; disintegration inhibitors such as saccharose, stearic acid, cocoa butter, and hydrogenated oils; absorption enhancers such as sodium lauryl sulfate; humectants such as glycerol and starch; adsorbents such as starch, lactose, kaolin, bentonite, and colloidal silicic acid; lubricants such as purified talc, stearic acid salts, powdered boric acid, and polyethylene glycol; and the like. Tablets may be optionally provided with general coatings to provide sugar-coated tablets, gelatin-coated tablets, enteric-coated tablets, film-coated tablets, double-layer tablets, multi-layer tablets, and the like.

When the preparation is prepared in the form of a pill, which is a solid oral preparation, examples of usable carriers include excipients such as glucose, lactose, starch, cacao butter, hydrogenated vegetable oils, kaolin, and talc; binders such as powdered gum arabic, powdered tragacanth, and gelatin; disintegrators such as laminaran and agar; and the like.

When the preparation is prepared in the form of a capsule, which is a solid oral preparation, it is prepared by mixing the active ingredient with one or more carriers mentioned above, and filling a hard capsule, a soft capsule, or the like with the mixture.

When the preparation is a liquid preparation, it may take the form of water-based or oil-based suspension, solution, syrup, or elixir, and can be prepared according to a common method, using one or more generally used additives.

When the preparation is prepared in the form of an injection, examples of usable carriers include diluents such as water, ethyl alcohol, macrogol, propylene glycol, ethoxylated isostearyl alcohol, polyoxylated isostearyl alcohol, and polyoxyethylene sorbitan fatty acid esters; pH-adjusters such as sodium citrate, sodium acetate, and sodium phosphate; buffers such as dipotassium phosphate, trisodium phosphate, sodium hydrogen phosphate, and sodium citrate; stabilizers such as sodium pyrosulfite, EDTA, thioglycolic acid, and thiolactic acid; saccharides such as mannitol, inositol, maltose, sucrose, and lactose for use as binders in freeze-drying; and the like. In this case, glucose or glycerol may be incorporated in the pharmaceutical preparation in an amount sufficient to prepare an isotonic solution. General solubilizing agents, soothing agents, topical anesthetics, etc., may also be added to the solution. Subcutaneous, intramuscular, and intravenous injections can be prepared according to common methods by adding these carriers.

When the preparation is prepared in the form of a drop, it can be prepared by dissolving the compound to be administered in an isotonic electrolyte infusion preparation, such as physiological saline or Ringer's solution.

In the cases where the pyridoxamine compound or the preparation containing the pyridoxamine compound, and the thiamine compound or the preparation containing the thiamine compound, are individually packaged as separate preparations and used in combination at use ((ii) and (iv) in the description of the phrase "formed by combining" described above), the pyridoxamine compound or the preparation containing the pyridoxamine compound can be administered before the start of or in parallel with administration of the thiamine compound or the preparation containing the thiamine compound. In another embodiment, the thiamine compound or the preparation containing the thiamine compound can be administered before the start of or in parallel with administration of the pyridoxamine compound or the preparation containing the pyridoxamine compound. Of course, the pyridoxamine compound or the preparation containing the pyridoxamine compound, and the thiamine compound or the preparation containing the thiamine compound, can also be administered at the same time.

When the pyridoxamine compound or the preparation containing the pyridoxamine compound is administered before the start of administration of the thiamine compound or the preparation containing the thiamine compound, administration of the pyridoxamine compound or the preparation containing the pyridoxamine compound can be initiated within the 3-day period immediately before the start of administration of the thiamine compound or the preparation containing the thiamine compound. Administration of the pyridoxamine compound or the preparation containing the pyridoxamine compound can be preferably initiated within the 2-day period immediately before, more preferably within the 24-hour period immediately before, even more preferably within the 12-hour period immediately before, and most preferably within the 3-hour period immediately before, the start of administration of the thiamine compound or the preparation containing the thiamine compound.

When the thiamine compound or the preparation containing the thiamine compound is administered before the start of administration of the pyridoxamine compound or the preparation containing the pyridoxamine compound, administration of the thiamine compound or the preparation containing the thiamine compound can be initiated within the 3-day period immediately before, preferably within the 2-day period immediately before, more preferably within the 24-hour period immediately before, even more preferably within the 12-hour period immediately before, and most preferably within the 3-hour period immediately before, the start of administration of the pyridoxamine compound or the preparation containing the pyridoxamine compound.

The administration period for the pyridoxamine compound or the preparation containing the pyridoxamine compound, and the administration period for the thiamine compound or the preparation containing the thiamine compound are as described above.

When the pyridoxamine compound or the preparation containing the pyridoxamine compound is administered in parallel with administration of the thiamine compound or the preparation containing the thiamine compound, the administration includes the following embodiments, as described above: (a) administration of the pyridoxamine compound or the preparation containing the pyridoxamine compound, and administration of the thiamine compound or a preparation containing the thiamine compound, are initiated at the same time; (b) administration of the pyridoxamine compound or the preparation containing the pyridoxamine compound is initiated before the start of administration of the thiamine compound or the preparation containing the thiamine compound; and (c) administration of the thiamine compound or the preparation containing the thiamine compound is initiated before the start of administration of the pyridoxamine compound or the preparation containing the pyridoxamine compound. It is preferable that (a) administration of the pyridoxamine compound or the preparation containing the pyridoxamine compound, and administration of the thiamine compound or the preparation containing the thiamine compound, be initiated at the same time. The phrase "administered in parallel" as used herein means that a state in which two or more active ingredients derived from different preparations are present together in the body is formed regardless of whether the preparations are administered at the same time. For example, if preparation B is administered after the start of administration of preparation A, when administration of preparation B forms a state in which the active ingredient of preparation B is present together with the active ingredient of preparation A present in the body with the active ingredient of preparation A being present from an earlier point, preparation A and preparation B can be described as being administered in parallel.

The combination drug in which the pyridoxamine compound and the thiamine compound are contained in the same preparation is a drug comprising both the pyridoxamine compound and the thiamine compound. Further, the combination drug may be prepared by using these compounds in combination with one or more carriers or additives for preparations described above.

The ratio of the thiamine compound to the pyridoxamine compound is not particularly limited, and the weight ratio of thiamine compound:pyridoxamine compound is, for example, 1:1 to 1:500, preferably 1:5 to 1:60, and more preferably 1:10 to 1:50.

Depending on the dosage form, the prepared combination drug may be administered once a day such that the daily doses of the pyridoxamine compound and the thiamine compound fall within the above ranges. If necessary, the prepared combination drug may be administered in two, three, four, or five portions a day, and preferably two or three portions a day, such that the daily doses fall within the above ranges.

The combination drug can be administered by oral administration or parenteral administration (intramuscular injection, subcutaneous injection, intravascular administration, rectal administration, transnasal administration, transpulmonary administration, etc.). The dosage forms can be prepared according to the preparation methods described above.

The pharmaceutical composition of the present invention can be administered for the prevention and/or treatment of vitamin B1 deficiency. The vitamin B1 deficiency is preferably, for example, vitamin B1 deficiency caused by administration of a pyridoxamine compound. Diagnosis of vitamin B1 deficiency can be made by measuring the concentration of vitamin B1 in blood also including blood cells (also called "whole blood") by a known method. For example, according to measurement using LC/MS/MS of SRL Inc., the reference value of the blood (whole blood) vitamin B1 concentration is 24 to 66 ng/mL. Thus, as the blood vitamin B1 concentration in a subject approaches the lower region of reference value range, the subject shows a greater tendency to vitamin B1 deficiency. The blood vitamin B1 concentration in such a subject is, for example, 30 ng/mL or less, preferably 25 ng/mL or less, and more preferably less than 24 ng/mL. The vitamin B1 concentration as used herein refers to the concentration of total vitamin B1, including thiamine and a phosphoric acid ester (thiamine diphosphate), which is an in vivo metabolite of thiamine.

In addition, for example, even when the blood vitamin B1 concentration in a subject is within the reference value range, in particular, when it exceeds 30 ng/mL, or even when the vitamin B1 concentration in a subject is unknown, the subject can be diagnosed with vitamin B1 deficiency also from the onset of at least one symptom selected from the group consisting of beriberi, axial optic neuritis, polyneuritis, Wernicke's encephalopathy, decreased appetite, and digestion disorders.

In another embodiment, the pharmaceutical composition of the present invention can be used for the prevention and/or treatment of at least one disease or symptom (vitamin B1 deficiency) selected from the group consisting of beriberi, axial optic neuritis, polyneuritis, Wernicke's encephalopathy, decreased appetite, and digestion disorders, all of which can be caused when a pyridoxamine compound or a preparation containing a pyridoxamine compound is administered at a daily dose of 300 mg or more calculated as pyridoxamine, preferably at least one disease or symptom (vitamin B1 deficiency) selected from the group consisting of axial optic neuritis, polyneuritis, and Wernicke's encephalopathy, even more preferably Wernicke's encephalopathy. The onset of Korsakoff's syndrome, which is a sequela of Wernicke's encephalopathy, can also be prevented by preventing and/or treating Wernicke's encephalopathy.

The pharmaceutical composition of the present invention can be preferably administered to a patient with an AGE-related disease. The AGE-related disease refers to a state in which the AGE level in the serum or plasma is near, equal to, or exceeds the upper limit of the reference value range measured by a standard measurement method for AGEs, regardless of whether the disease is one that develops due to accumulation of AGEs or the AGE level is high due to the disease.

Examples of AGEs include pentosidine, crossline, imidazolone, carboxymethyllysine (CML), carboxymethylarginine (CMA), pyrraline, and the like.

Among these, the reference values of pentosidine and carboxymethyllysine in the serum or plasma are, for example, as follows.

Pentosidine

The reference value of the plasma pentosidine concentration measured using FSK pentosidine (Fushimi Pharmaceutical Co., Ltd.) by the ELISA method is 9.15 to 43.1 ng/mL. The reference value of the plasma pentosidine concentration measured using LC/MS/MS after the plasma is treated with an acid according to Item 2-2 of the Reference Experiment Example described below is also the same as the above reference value measured by the ELISA method. Thus, when the plasma pentosidine concentration is more than 45 ng/mL, preferably more than 50 ng/mL, and more preferably more than 55 ng/mL, this state can be defined as an AGE-related disease.

Carboxymethyllysine (CML)

The reference value of the plasma CML concentration measured by the ELISA method is 2.65 to 6.23 µg/mL. Thus, when the plasma CML concentration is more than 6.5 µg/mL, preferably more than 7.0 µg/mL, and more preferably more than 7.5 µg/mL, this state can be defined as an AGE-related disease.

The AGE-related disease can also include a state in which the serum and/or plasma concentration of 3-deoxyglucosone (3-DG), glyoxal (GO), methylglyoxal (MGO), or the like, none of which are AGEs themselves, but precursors of AGEs, is high.

In addition, when the pharmaceutical composition of the present invention is applied to a subject, the pharmaceutical composition of the present invention can be administered to a subject in which the plasma pentosidine concentration is more than 30 ng/mL, and preferably more than 35 ng/mL; a subject in which the plasma CML concentration is more than 4.5 µg/mL, and preferably more than 5.5 µg/mL; or a subject in which the plasma 3-DG concentration is more than 12.00 ng/mL, and preferably more than 16.00 ng/mL, in order to initiate treatment prophylactically and/or earlier. Further, since the plasma methylglyoxal (MGO) concentration in healthy subjects is 123.0±37.0 nmol/L and the plasma methylglyoxal (MGO) concentration in type 2 diabetes patients is 189.3±38.7 nmol/L, the pharmaceutical composition of the present invention can also be administered to a subject in which the plasma MGO concentration is more than 160 nmol/L, and preferably more than 180 nmol/L.

Further, other examples of AGE-related diseases for which the pharmaceutical composition of the present invention is administered include diabetes, diabetic complications (e.g., diabetic retinopathy, diabetic keratopathy, diabetic nephropathy, and diabetic neuropathy), chronic renal failure, complications of chronic renal failure (e.g., vascular disorders and bone disorders), nephropathy, nephritis, inflammatory diseases, atherosclerosis, age-related eye diseases (e.g., cataracts, pingueculae, sheroid degeneration, and macular degeneration), neurodegenerative diseases (e.g., Parkinson's disease, amyotrophic lateral sclerosis, and Alzheimer-type dementia), alcoholism, autism, schizophrenia, malignant melanoma, osteoporosis, deterioration of the peritoneum in peritoneal dialysis, chronic rheumatism, atopic dermatitis, and the like. The disease for which the pharmaceutical composition of the present invention is administered is more preferably at least one disease selected from the group consisting of diabetes, diabetic retinopathy, diabetic keratopathy, diabetic nephropathy, diabetic neuropathy, chronic renal failure, atherosclerosis, cataracts, macular degeneration, alcoholism, osteoporosis, deterioration of the peritoneum in peritoneal dialysis, and schizophrenia, even more preferably at least one disease selected from the group consisting of diabetic retinopathy, diabetic keratopathy, diabetic nephropathy, diabetic neuropathy, chronic renal failure, deterioration of the peritoneum in peritoneal dialysis, and schizophrenia, and most preferably schizophrenia.

In addition, the pharmaceutical composition of the present invention can also be applied to diseases that develop and/or progress with aging. Examples of such diseases include vascular diseases (e.g., atherosclerosis, medial sclerosis, and arteriolosclerosis), musculoskeletal disease (e.g., osteoporosis, rheumatoid arthritis, and ossification of the posterior longitudinal ligament), nervous system diseases (e.g., Parkinson's disease, amyotrophic lateral sclerosis, and Alzheimer-type dementia), ophthalmologic diseases (cataracts, pingueculae, sheroid degeneration, and macular degeneration), skin diseases (malignant tumors, senile xerosis, and senile lentigo), and the like.

2. Pharmaceutical Product or Pharmaceutical Composition Used in Combination with Thiamine Compound In an embodiment, the present invention includes a pharmaceutical product or pharmaceutical composition comprising a pyridoxamine compound, the pharmaceutical product or the pharmaceutical composition being used in combination with a thiamine compound. The pharmaceutical product or the pharmaceutical composition is used for preventing and/or treating an AGE-related disease. Specifically, the pharmaceutical product or the pharmaceutical composition can be used for preventing and/or treating an AGE-related disease.

(1) Pharmaceutical Product Used in Combination with Thiamine Compound

The pharmaceutical product of the present invention comprises the following (A) and (B):

(A) a packaged pharmaceutical composition containing at least one pyridoxamine compound selected from the group consisting of pyridoxamine and pharmaceutically acceptable salts thereof as an active ingredient; and (B) at least one document selected from the group consisting of a package insert, directions, instructions, and a product label, each stating that the pharmaceutical composition is used in combination with at least one thiamine compound selected from the group consisting of thiamine, derivatives thereof, and pharmaceutically acceptable salts thereof, for the treatment of an AGE-related disease.

"Pyridoxamine," "pharmaceutically acceptable salts thereof," and "pharmaceutical composition" in (A) are as explained in the "1. Combination pharmaceutical composition" section above; therefore, the above descriptions can also be applied here. The daily dose of the pyridoxamine compound, the method for administering the pyridoxamine compound, and the subject to which the pyridoxamine compound is administered (subject) are also as explained in the "1. Combination pharmaceutical composition" section above; therefore, the above descriptions can also be applied here.

In addition, "thiamine," "derivatives thereof," "pharmaceutically acceptable salts thereof," and "AGE-related disease" in (B) are as explained in the "1. Combination pharmaceutical composition" section above; therefore, the above descriptions can also be applied here. The dose of the thiamine compound used in combination with the pyridoxamine compound, the method for administering the thiamine compound, and the subject to which the thiamine compound is administered (subject) are also as explained in the "1. Combination pharmaceutical composition" section above; therefore, the above descriptions can also be applied here.

The term "package insert" in (B) means an official document that is provided with a medicament, gives necessary information for appropriate use of the medicament, and corresponds to Tenpu Bunsho (also referred to as nogaki) in accordance with the Japan Pharmaceutical Affairs Act, Summary of Product Characteristics (SPC or SmPC) in accordance with EU Directives, US Package Insert (USPI) in accordance with United States Federal Regulations, and equivalent documents in other countries.

The items described in these documents are specifically prescribed in Articles 52, 54, 68-4, etc., in the Pharmaceutical Affairs Act (see, if necessary, Notification Nos. 606 and 607 of Pharmaceutical Affairs Bureau dated Apr. 25, 1997, and/or related notifications) for Tenpu Bunsho in Japan, in Directive 2001/83/EC Article 11, etc., (see, if necessary, A Guideline on SmPC and/or related guidelines) for Summary of Product Characteristics in the EU, and in 21 CFR 201.100, etc., (see, if necessary, 21 CFR 201.57 and/or related Federal Regulations) for US Package Insert in the United States. The items generally include information on, for example, indications, dosage and administration, method of administration, warnings, and/or contraindications.

In the United States, 21 CFR 201 Subpart B requires that in addition to the US Package Insert, a "label," "labeling," or "labelling" contains some or all of the contents described in the US Package Insert. Here, "label" means a label directly provided on a container, and "labeling" or "labelling" means the concept encompassing the label, printing on a package, printed matter provided with a product, and the like.

The document of (B) above is not limited to a package insert or a product label, and documents such as directions and instructions are also included in the document of (B) above, regardless of their format or name, as long as they state that (A) the pharmaceutical composition is used in combination with a thiamine compound for the treatment of an AGE-related disease.

For the expression "packaged" in (A), the term "package" means a containing instrument for containing a pharmaceutical composition comprising a pyridoxamine compound. Examples of such an instrument include containers, wrappers, inner seals, and the like. The package is not limited to these instruments, and examples include cans, bottles, boxes, ampoules, vials, tubes, unit dose containers, paper, cloth, plastics, plastic bags, SP sheets, PTP sheets, plastic containers, and the like. "Packaged pharmaceutical composition" in (A) means that the pharmaceutical composition comprising at least a pyridoxamine compound is contained in a containing instrument such as those described above. The packaged pharmaceutical composition is combined with at least one document selected from the group consisting of the above-mentioned package insert, product label (including one corresponding to a label, labeling, or labelling in the United States), directions, instructions, and the like, and is generally packaged in an outer container or an outer wrapper, and distributed to the market.

(2) Pharmaceutical Composition Used in Combination with Thiamine Compound

The pharmaceutical composition of the present invention comprises at least one pyridoxamine compound selected from the group consisting of pyridoxamine and pharmaceutically acceptable salts thereof as an active ingredient, the pharmaceutical composition being used in combination with at least one thiamine compound selected from the group consisting of thiamine, derivatives thereof, and pharmaceutically acceptable salts thereof, for the treatment of an AGE-related disease at a daily dose of 300 mg or more calculated as pyridoxamine.

The terms "pyridoxamine," "pharmaceutically acceptable salts thereof," "pharmaceutical composition," "thiamine," "derivatives thereof," "pharmaceutically acceptable salts thereof," and "AGE-related disease" here are as explained in the "1. Combination pharmaceutical composition" section above; therefore, the above descriptions can also be applied here. The daily dose of the pyridoxamine compound, the method for administering the pyridoxamine compound, the subject to which the pyridoxamine compound is administered (subject), the dose of the thiamine compound used in combination with the pyridoxamine compound, the method for administering the thiamine compound, and the subject to which the thiamine compound is administered (subject) are also as explained in the "1. Combination pharmaceutical composition" section above; therefore, the above descriptions can also be applied here.

3. Method for Preventing and/or Treating AGE-Related Disease

The method for preventing and/or treating an AGE-related disease of the present invention comprises the following administering step:
simultaneously or separately administering, to a subject,
(1) at least one pyridoxamine compound selected from the group consisting of pyridoxamine and pharmaceutically acceptable salts thereof, and
(2) at least one thiamine compound selected from the group consisting of thiamine, derivatives thereof, and pharmaceutically acceptable salts thereof, the daily dose of the pyridoxamine compound being 300 mg or more calculated as pyridoxamine.

The terms "pyridoxamine," "pharmaceutically acceptable salts thereof," "thiamine," "derivatives thereof," "pharmaceutically acceptable salts thereof," and "AGE-related disease" here are as explained in the "1. Combination pharmaceutical composition" section above; therefore, the above descriptions can also be applied here. The daily dose of the pyridoxamine compound, the method for administering the pyridoxamine compound, the subject to which the pyridoxamine compound is administered (subject), the dose of the thiamine compound used in combination with the pyridoxamine compound, the method of administering the thiamine compound, and subject to which the thiamine compound is administered (subject) are also as explained in the "1. Combination pharmaceutical composition" section above; therefore, the above descriptions can also be applied here.

4. Method for Preventing and/or Treating Vitamin B1 Deficiency Caused by Administration of Pyridoxamine Compound The method for preventing and/or treating vitamin B1 deficiency of the present invention is a method for preventing and/or treating vitamin B1 deficiency caused by administration of a pyridoxamine compound, the method comprising administering (1) at least one pyridoxamine compound selected from the group consisting of pyridoxamine and pharmaceutically acceptable salts thereof and (2) at least one thiamine compound selected from the group consisting of thiamine, derivatives thereof, and pharmaceutically acceptable salts thereof, to a subject simultaneously or separately, the serum or plasma concentration of at least one compound selected from the group consisting of pentosidine, carboxymethyllysine, and 3-deoxyglucosone in the subject before administration of the pyridoxamine compound being as follows:
(a) pentosidine: 45 ng/ml or more
(b) carboxymethyllysine: 6.5 µg/ml or more
(c) 3-deoxyglucosone: 20 ng/ml or more.

The terms "vitamin B1 deficiency," "pyridoxamine," "pharmaceutically acceptable salts thereof," "thiamine," "derivatives thereof," and "pharmaceutically acceptable salts thereof" here are as explained in the "1. Combination pharmaceutical composition" section above; therefore, the above descriptions can also be applied here. The daily dose of the pyridoxamine compound, the method for administering the pyridoxamine compound, the subject to which the pyridoxamine compound is administered (subject), the dose of the thiamine compound used in combination with the pyridoxamine compound, the method for administering the thiamine compound, and the subject to which the thiamine compound is administered (subject) are also as explained in the "1. Combination pharmaceutical composition" section above; therefore, the above descriptions can also be applied here.

The details are as described below.

The prevention and/or treatment method is applied to a subject to which the pyridoxamine compound is administered at a daily dose of, for example, 300 mg or more calculated as pyridoxamine, as described in the "1. Combination pharmaceutical composition" section above. The minimum dose and the maximum dose are in accordance with the "1. Combination pharmaceutical composition" section above.

Further, the subject to which the prevention and/or treatment method is applied is, for example, a subject with an AGE-related disease in which the serum and/or plasma concentration of, for example, pentosidine, crossline, imidazolone, carboxymethyllysine (CML), carboxymethylarginine (CMA), pyrraline, 3-deoxyglucosone (3-DG), glyoxal (GO), and/or methylglyoxal (MGO) is near, equal to, or exceeds the upper limit of the reference value range of the compound measured by a standard measurement method for the compound as described above. The subject to which the prevention and/or treatment method is applied is preferably a subject in which the serum or plasma concentration of at least one compound selected from the group consisting of pentosidine, carboxymethyllysine, and 3-deoxyglucosone is near, equal to, or exceeds the upper limit of the reference value range of the compound measured by a standard measurement method for the compound.

For example, when pentosidine is used as an index, since the reference value of the plasma pentosidine concentration measured using, for example, FSK pentosidine (Fushimi Pharmaceutical Co., Ltd.) using the ELISA method is 9.15 to 43.1 ng/mL, a subject in which the plasma pentosidine concentration is more than 45 ng/mL, more preferably more than 50 ng/mL, and even more preferably more than 55 ng/mL can be determined to be a subject to whom the prevention and/or treatment method is applied.

When carboxymethyllysine (CML) is used as an index, since the reference value of the plasma CML concentration measured by, for example, the ELISA method is 2.65 to 6.23 µg/mL, a subject in which the plasma CML concentration is more than 6.5 µg/mL, more preferably more than 7.0 µg/mL, and even more preferably more than 7.5 µg/mL, can be determined to be a subject to whom the prevention and/or treatment method is applied.

Further, when the plasma 3-DG concentration is used as an index, since the reference value of the plasma 3-DG concentration measured by, for example, the HPLC method is 3.76 to 18.14 ng/mL, a subject in which the plasma 3-DG concentration is more than 20.00 ng/mL, more preferably more than 22.00 ng/mL, and even more preferably more than 25.00 ng/mL, can be determined to be a subject to whom the prevention and/or treatment method is applied.

Examples of subjects to whom the prevention and/or treatment method is applied include those suffering from, for example, diabetes, diabetic complications (e.g., diabetic retinopathy, diabetic keratopathy, diabetic nephropathy, and diabetic neuropathy), chronic renal failure, complications of chronic renal failure (e.g., vascular disorders and bone disorders), nephropathy, nephritis, inflammatory diseases, atherosclerosis, age-related eye diseases (e.g., cataracts, pingueculae, sheroid degeneration, and macular degeneration), neurodegenerative diseases (e.g., Parkinson's disease, amyotrophic lateral sclerosis, and Alzheimer-type dementia), alcoholism, autism, schizophrenia, malignant melanoma, deterioration of the peritoneum in peritoneal dialysis, chronic rheumatism, and/or atopic dermatitis. The subject is more preferably a subject suffering from at least one disease selected from the group consisting of diabetes, diabetic retinopathy, diabetic keratopathy, diabetic nephropathy, diabetic neuropathy, chronic renal failure, atherosclerosis, cataracts, macular degeneration, alcoholism, deterioration of the peritoneum in peritoneal dialysis, and schizophrenia, even more preferably a subject suffering from at least one disease selected from the group consisting of diabetic retinopathy, diabetic keratopathy, diabetic nephropathy, diabetic neuropathy, chronic renal failure, deterioration of the peritoneum in peritoneal dialysis, and schizophrenia, and most preferably a subject suffering from schizophrenia.

The pharmaceutical composition of the present invention can also be applied to diseases that develop and/or progress with aging. Examples of such diseases include vascular diseases (e.g., atherosclerosis, medial sclerosis, and arteriolosclerosis), musculoskeletal diseases (e.g., osteoporosis, rheumatoid arthritis, and ossification of the posterior longitudinal ligament), nervous system diseases (e.g., Parkinson's disease, amyotrophic lateral sclerosis, and Alzheimer-type dementia), ophthalmologic diseases (cataracts, pingueculae, sheroid degeneration, and macular degeneration), skin diseases (malignant tumors, senile xerosis, and senile lentigo), and the like.

The definition of vitamin B1 deficiency is as described in the "1. Combination pharmaceutical composition" section above.

Prevention and/or treatment of vitamin B1 deficiency caused by administration of a pyridoxamine compound can be performed by administering the combination pharmaceutical composition described in the "1. Combination pharmaceutical composition" section above. The method for preparing the preparation and the administration method can be performed in accordance with the "1. Combination pharmaceutical composition" section above.

EXAMPLES

The present invention will be described in more detail below with reference to Reference Experiment Example and Experiment Examples; however, the present invention is not limited to these Examples.

Reference Experiment Example

Effect of Administration of Pyridoxamine Compound on Schizophrenia Patients
1. Subject and Drug Administration The target subjects (subjects) of this test (administration of a pyridoxamine compound; hereinafter, this is also referred to as "drug administration") were patients who were diagnosed with schizophrenia and met all of the following conditions (1) to (3):
(1) schizophrenia patient meeting all of the following:
(a) patient meeting SM-IV-TR diagnostic criteria from not less than 1 year before the time of consent to drug administration,
(b) patient in whom the blood pentosidine concentration is 55.2 ng/mL or more, and
(c) patient in whom the total PANSS score in the observation period and at the time of baseline is 60 or more;
(2) schizophrenia patient who, or whose legally authorized representative, gave informed consent and from whom written consent to drug administration was obtained; and
(3) inpatient with schizophrenia who was 20 years of age or older but less than 65 years of age at the time of consent to drug administration.

Drug administration was initiated for nine subjects from whom consent was obtained. The observation period was defined as the period from the day on which consent was obtained (Day −14) to the day 2 weeks after the day of consent (Day 0), and the initial day of drug administration was defined as Day 1. The data of Day 1 is data immediately before the start of administration of the pyridoxamine compound. The drug administration period was defined as the 24-week period from the start of drug administration (Day 1 to Day 169).

In the drug administration, pyridoxamine dihydrochloride was used as the pyridoxamine compound and orally administered in an amount of 1200 mg, 1800 mg, or 2400 mg per day (administered three times a day, morning, noon, and before bedtime, in an amount of 400 mg, 600 mg, or 800 mg each time). In the drug administration period, the dose was increased or decreased within the above range according to the condition of each patient.

2. Evaluation of Effect of Administration of Pyridoxamine Compound

The effect of administration of the pyridoxamine compound (drug administration) was evaluated according to the Positive and Negative Syndrome Scale (PANSS) score and the concentration of pentosidine in blood of the schizophrenia patients.

2-1. PANSS Score

The PANSS score was determined by SCI-PANSS, which uses a structured interview, according to the Positive and Negative Syndrome Scale (PANSS) manual (translated by Hiroshi Yamada, Kanji Masui, and Hirotsugu Kikumoto; Tokyo: Seiwa Shoten Co., Ltd., 1991). An interview for evaluation was conducted for 30 evaluation items. Each item was scored on a scale of 1 to 7. The sum of the scores was calculated, and the difference between the PANSS score on Day 1 and the PANSS score on each test day was determined. A negative numerical value indicates that a symptom is improved. The subjects were prohibited from taking hypnotic drugs or antianxiety drugs within 4 hours before PANSS evaluation.

As shown in Table 1, the results reveal that the PANSS score decreased by an average of 3.7 points on day 15 after the start of drug administration (Day 15). Further, the PANSS score decreased by an average of 12.2 points on day 113 after the start of drug administration (Day 113), indicating that the symptom of schizophrenia was notably improved by administration of the pyridoxamine compound.

TABLE 1

Change from baseline in total PANSS score at each evaluation time point (FAS)

| Period | | Day 15 (2 w) | Day 29 (4 w) | Day 57 (8 w) | Day 85 (12 w) | Day 113 (16 w) | Day 141 (20 w) | Day 169 (24 w) | Final evaluation time point |
|---|---|---|---|---|---|---|---|---|---|
| Number of subjects | | 9 | 9 | 9 | 9 | 9 | 8 | 8 | 9 |
| Mean change | | −3.7 | −4.4 | −5.0 | −7.3 | −12.2 | −9.6 | −11.4 | −10.6 |
| Summary statistics | Standard deviation | 16.99 | 18.35 | 22.89 | 23.67 | 23.04 | 25.96 | 27.05 | 25.42 |
| | Median | 3.0 | 1.0 | 1.0 | −3.0 | −5.0 | −1.5 | −7.5 | −5.0 |
| | Minimum | −44 | −49 | −58 | −65 | −69 | −64 | −69 | −69 |
| | Maximum | 12 | 10 | 13 | 21 | 8 | 17 | 14 | 14 |

The above results show that administration of the pyridoxamine compound is effective in improving the symptom of schizophrenia.

2-2. Blood Pentosidine Concentration (1) Method (1-1) Preparation of Reagents 12N hydrochloric acid: stock solution (for automatic amino acid analysis; Wako Pure Chemical Industries, Ltd.)

6N hydrochloric acid (prepared at the time of use): prepared by adding, to Milli-Q water, 12N hydrochloric acid in an amount equal to the amount of Milli-Q water, and mixing them Pentosidine standard: synthetic pentosidine (14.3 pmol/ml, stored at −30° C.)

Solution A in mobile phase for HPLC (0.1% TEA/distilled water): prepared by adding 1.95 ml of trifluoroacetic acid (TFA; Wako Pure Chemical Industries, Ltd.) to 3 L of distilled water (for high-performance liquid chromatography; Wako Pure Chemical Industries, Ltd.), mixing them, and degassing for 20 minutes Solution B in mobile phase for HPLC (0.08% TFA/80% acetonitrile): prepared by mixing 500 ml of distilled water (same as described above), 2 L of acetonitrile (for high-performance liquid chromatography; Wako Pure Chemical Industries, Ltd.), and 1.3 ml of TFA and degassing for 20 minutes (1-2) Preparation of Measurement Samples In the morning 20 days before the start of drug administration (Day −20), on the initial day of drug administration (Day 1), and on Day 15, Day 29, Day 85, and Day 169 after the start of drug administration, blood was drawn from the nine subjects above before administration of the drug. The plasma was freeze-preserved until measurement. The plasma pentosidine concentration was measured according to the method described below.

The freeze-preserved plasma was left to thaw, mixed by inversion, and centrifuged (3,000 rpm, 10 min, 4° C.) to remove insoluble matter. 50 µl of the plasma prepared above and 50 µl of 12N hydrochloric acid were placed in a glass sample tube (Part No. WAT007571; Waters) and mixed. 100 µl of 6N hydrochloric acid was added to the bottom of a separately prepared capped reaction vial (Part No. JLC 007363; Waters), and the glass sample tube was gently placed in the vial. The cap of the capped reaction vial was tightly closed, and the vial was spun down (1,000 rpm, 3 min). The atmosphere in the capped reaction vial was replaced with nitrogen five times, and treatment was performed at 110° C. for 16 hours in an oven for hydrolysis to hydrolyze the plasma component. After the end of the hydrolysis reaction, the glass sample tube was removed from the capped reaction vial, and 80 µl of an aqueous 5N sodium hydroxide solution was added to the sample tube to neutralize the plasma. Subsequently, the neutralized solution was concentrated to dryness with a centrifugal concentrator. The dry solid was dissolved in 200 µl of Milli-Q water and subjected to centrifugal filtration at 8,000 rpm for 3 minutes using an Ultrafree (registered trademark)-MC centrifugal filter unit (CAT No. UFC30HV0; pore size: 0.45 µm; Merck Millipore Corporation). The obtained filtrate ("sample") was stored at 4° C. protected from light until pentosidine measurement.

(1-3) HPLC Analysis of Samples

The samples prepared as described above were diluted 10-fold with Milli-Q water (diluted samples). As a pentosidine standard, 14.3 pmol/ml of a synthetic pentosidine solution was prepared and diluted 2-fold with Milli-Q water at the time of analysis (diluted pentosidine standard). The diluted samples and the diluted pentosidine standard were subjected to HPLC (HPLC apparatus produced by Shimadzu Science) under the following conditions, and analysis of pentosidine was performed with a fluorescence measuring device (SLC-10Avp; equipped with UV and fluorescence detectors). The pentosidine concentrations in the sample was determined by proportionally calculating the area of the diluted sample and the area of the diluted pentosidine standard according to the following equation and multiplying them by the dilution factors.

HPLC analysis conditions
Column: puresil 5µ C18 120 Å 4.6×250 mm (Waters)
Mobile phase A: 0.1 v/v % TFA/distilled water
Mobile phase B: 0.08 v/v % TFA/80 v/v % acetonitrile
Gradient: 2.0 v/v % to 8.0 v/v % (mobile phase B)/25 min
Flow rate: 0.800 ml/min
Column temperature: 30° C.
Detection: fluorescence Ex 335 nm, Em 385 nm
Injection volume: 20 µl Pentosidine amount(nmol/ml)={(diluted sample area×7.15)/(diluted pentosidine standard area×2)}/1000    Equation (2) Results FIG. 1 shows the results. As shown in FIG. 1, it was observed that the blood pentosidine concentration at the end of administration of the pyridoxamine compound (Day 169) was lower than that on Day 1 in at least seven subjects. The results of statistical analysis showed that the plasma pentosidine concentration was decreased by administration of the pyridoxamine compound.

The above results indicate that administration of pyridoxamine has the effect of decreasing the amount of pentosidine, i.e., the amount of advanced glycation end products (AGEs) in the body.

Experiment Example 1

Treatment for Vitamin B1 Deficiency that Occurs During Administration of Pyridoxamine Compound FIG. 2 shows protocols for drug administration, the whole blood vitamin B1 (VB1) amount, the serum pyridoxamine (PM) concentration, the serum pyridoxal (PL) concentration, and the serum pyridoxine (PN) concentration for two schizophrenia patients who developed vitamin B1 deficiency during administration of the pyridoxamine compound ("drug administration") (ID: No. 3 (age: 61 years old, body weight: 43 kg) and No. 6 (age: 62 years old, body weight: 44 kg)).

Measurement of the amount of vitamin B1 in whole blood (blood collection with heparin) was outsourced to SRL Inc., and the measurement was performed using LC/MS/MS.

Measurement of the serum pyridoxamine concentration, the serum pyridoxal concentration, and the serum pyridoxine concentration was outsourced to SRL Inc. or Mitsubishi Chemical Medience Corporation (now LSI Medience Corporation).

Pyridoxamine dihydrochloride was orally administered as a pyridoxamine compound to schizophrenia patients daily, three times a day (morning, noon, and before bedtime) in an amount of 400 mg or 600 mg each time (daily dose of pyridoxamine: about 830 mg or 1250 mg) according to the protocols shown in FIG. 2 (described as "PM dose (mg/one time)" in FIG. 2).

Since an epilepsy-like symptom appeared 6 weeks after the start of drug administration in the patient of ID No. 3, the patient underwent MRI of the brain, and findings suggestive of Wernicke's encephalopathy were obtained. The whole blood vitamin B1 amount in the patient at the time was 28 ng/mL, which was near the lower limit of the reference value range (24 to 66 ng/mL). From these results, it was suspected that the patient might develop vitamin B1 deficiency during drug administration. The serum pyridoxamine concentration in the patient 4 weeks after the start of drug administration was 1543 ng/mL, which was about 7700 times higher than that at the time of the start of drug administration. In addition, the serum pyridoxal concentration was 2357 ng/mL, which was about 380 times higher than that at the time of the start of drug administration. Immediately after the patient was suspected of having Wernicke's encephalopathy, oral administration of a thiamine compound (fursultiamine (Takeda Pharmaceutical Company Limited)) at a dose of 75 mg/day was initiated (administered once a day) and continued every day. As a result, the whole blood vitamin B1 amount increased to 135 ng/mL 12 weeks after the start of drug administration (6 weeks after the start of administration of the thiamine compound). Further, even though administration of the pyridoxamine compound was continued every day, the serum pyridoxamine concentration at the time was 23.2 ng/mL, and the serum pyridoxal concentration was 1179 ng/mL, both of which were lower than those 4 weeks after the start of drug administration. The symptom of Wernicke's encephalopathy disappeared 14 weeks after the start of drug administration (8 weeks after the start of administration of the thiamine compound).

The patient of ID No. 6 underwent MRI of the brain 9 weeks after the start of drug administration, and findings suggestive of Wernicke's encephalopathy were obtained. The whole blood vitamin B1 amount in the patient at the time was 25 ng/mL. The serum pyridoxamine concentration in the patient 8 weeks after the start of drug administration was 421 ng/mL, which was about 2100 times higher than that at the time of the start of drug administration. In addition, the serum pyridoxal concentration was 2968 ng/mL, which was about 850 times higher than that at the time of the start of drug administration. Immediately after the patient was suspected of having Wernicke's encephalopathy, intravenous administration of a thiamine compound (fursultiamine (Takeda Pharmaceutical Company Limited)) (300 mg/day) was performed, and then (from 10 weeks after the start of drug administration), oral administration of the thiamine compound at a dose of 100 to 50 mg/day was continued. As a result, the whole blood vitamin B1 amount increased to 150 ng/mL 11 weeks after the start of drug administration (3 weeks after the start of administration of the thiamine compound), and the symptom of Wernicke's encephalopathy also disappeared. At the time, the serum pyridoxamine concentration was 140 ng/mL, and the serum pyridoxal concentration was 3941 ng/mL.

These cases suggested the possibility that administration of a pyridoxamine compound in the treatment of schizophrenia causes vitamin B1 deficiency.

Experiment Example 2

Blood Kinetics of Pyridoxamine Compound

As described in Experiment Example 1 above, administration of a pyridoxamine compound increases not only the blood pyridoxamine concentration, but also the blood pyridoxal concentration. Rather, in blood, the pyridoxal concentration was higher than the pyridoxamine concentration. Thus, changes in the serum concentrations of pyridoxamine, pyridoxal, pyridoxine, and 4-pyridoxic acid after administration of a pyridoxamine compound were observed over time.

More specifically, 150 mg of pyridoxamine dihydrochloride was orally administered to each of six people with reduced renal function (subjects) (average age: 56 years old, average body weight: 67 kg). Blood was collected 0.5, 1, 1.5, 2, 2.5, 3, 4, 5, 6, 8, 10, and 12 hours after the administration, and the serums were collected. Measurement of the serum concentrations of pyridoxamine, pyridoxal, pyridoxine, and 4-pyridoxic acid was outsourced to Shin Nippon Biomedical Laboratories, Ltd.

Figure 3:
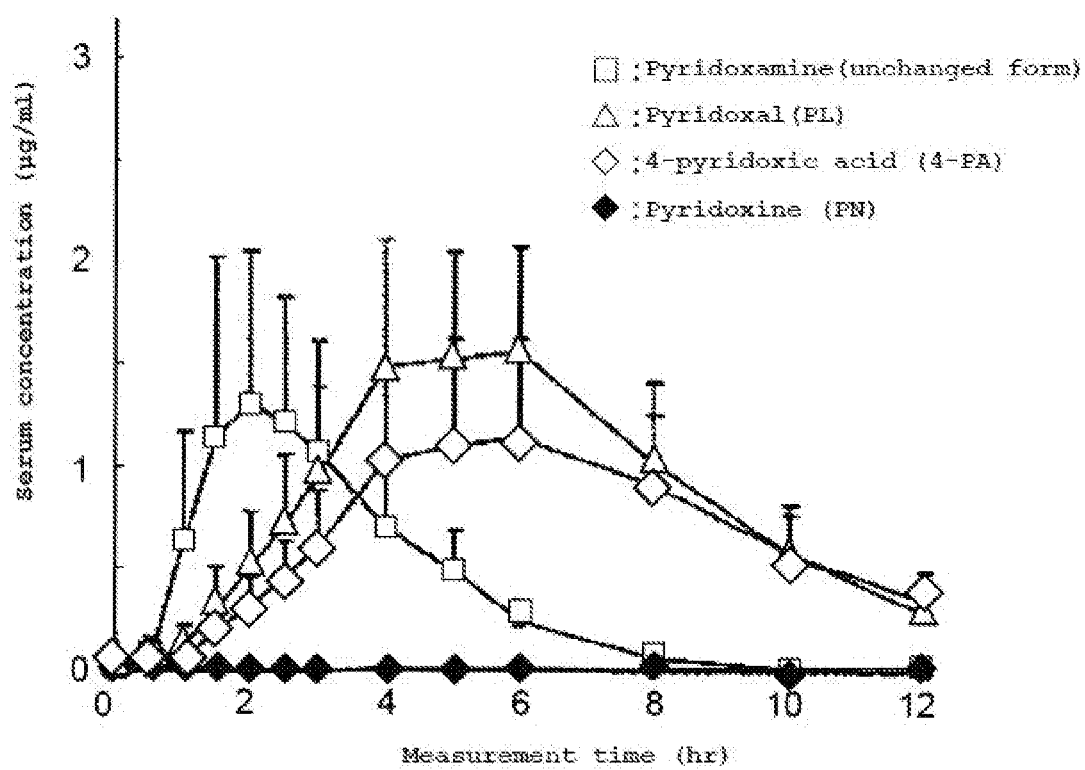
FIG. 3 shows changes in the serum concentrations of pyridoxamine (unchanged form: □), pyridoxal (PL: Δ), 4-pyridoxic acid (4-PA: ◇), and pyridoxine (PN: ♦) after administration of a pyridoxamine compound (pyridoxamine dihydrochloride) to six people with reduced renal function. The horizontal axis indicates time (hr) after administration of the pyridoxamine compound.

FIG. 3 shows the results. As shown in FIG. 3, the serum concentration of pyridoxamine (unchanged form: □) peaked 2 hours after administration of pyridoxamine and then decreased. The concentration of pyridoxal (PL: Δ) and the concentration of 4-pyridoxic acid (4-PA: ◇) peaked 4 to 6 hours after administration of pyridoxamine such that they replaced the peak of the pyridoxamine concentration. No large change in the concentration of pyridoxine (PN: ♦) was observed.

The above results revealed that most of the pyridoxamine compound absorbed in the body was converted to pyridoxal and 4-pyridoxic acid.

Experiment Example 3

Effect of Pyridoxamine and Pyridoxal on Whole Blood Vitamin B1 Concentration

Since the possibility that administration of a pyridoxamine compound causes vitamin B1 deficiency was suggested in Experiment Example 1 above, an in vitro test was performed to investigate whether a pyridoxamine compound decreases the whole blood vitamin B1 concentration. In addition, as described in Experiment Example 1 and Experiment Example 2, administration of a pyridoxamine compound increases not only the serum pyridoxamine concentration, but also the serum pyridoxal concentration, and thus, pyridoxamine and pyridoxal were both used as test substances for the investigation.

1. Method

Blood was collected from a human using EDTA•2K as an anticoagulant. In addition, pyridoxamine dihydrochloride (Sigma-Aldrich Japan) was used as pyridoxamine, and pyridoxal hydrochloride (Nacalai Tesque, Inc.) was used as pyridoxal. They were dissolved at 0.5, 5, and 50 mg/mL in physiological saline to prepare test solutions. 10 μL of each test solution was individually added per mL of the whole blood collected above (test samples). The final concentrations of each test substance in the test samples were 5, 50, 500 μg/mL. Further, a vehicle was prepared by adding 10 μl of physiological saline to 1 ml of the whole blood. The vehicle and the test samples were incubated at 37° C. for 1 hour or 16 hours and then immediately frozen. Measurement of the vitamin B1 concentrations in the whole blood before the start of the incubation to which neither the physiological saline nor any test solution was added (baseline: indicated by "BL" in FIG. 4), and in the vehicle and in each test sample after the incubation, was outsourced to SRL Inc., and the measurement was performed using LC/MS/MS.

2. Results

Figure 4:
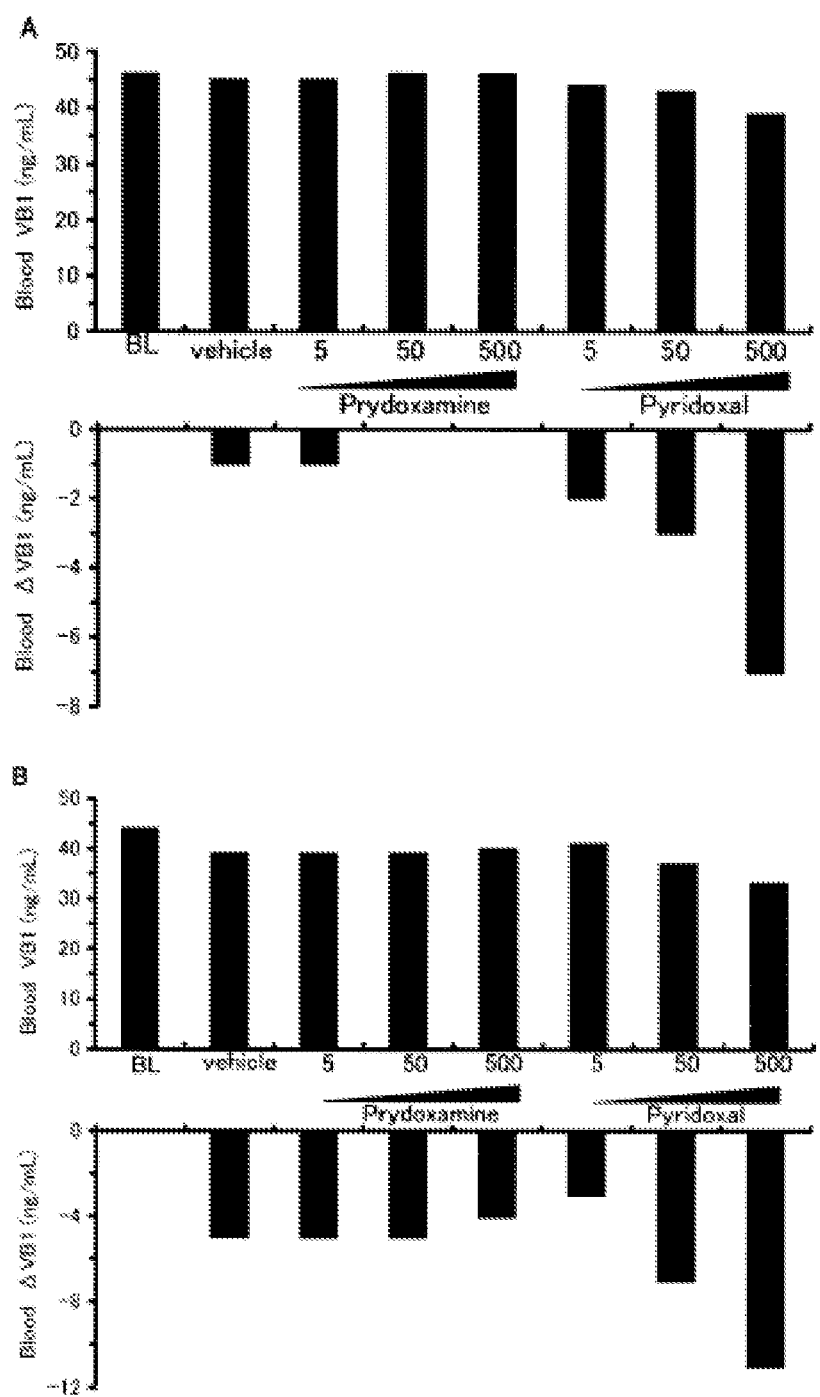
FIG. 4 shows changes in the vitamin B1 concentration in human whole blood (samples) to which pyridoxamine dihydrochloride (final concentrations: 5, 50, 500 μg/mL) or pyridoxal hydrochloride (final concentrations: 5, 50, 500 μg/mL) was added. Panel A in FIG. 4 shows measurement results of samples when incubation was performed for 1 hour, and Panel B shows measurement results of samples when incubation was performed for 16 hours. In each of Panel A and Panel B, the upper part shows the whole blood vitamin B1 concentration, and the lower part shows differences between the vitamin B1 concentration in human whole blood (before incubation) (BL: baseline) and the vitamin B1 concentration after incubation.

FIG. 4 shows the measurement results. Panel A and Panel B show the results 1 hour and 16 hours after the incubation, respectively. In each of Panel A and Panel B, the upper part shows the whole blood vitamin B1 concentration, and the lower part shows differences between the baseline whole blood vitamin B1 concentration and the vitamin B1 concentration after the incubation.

One hour after the incubation, no changes in the vitamin B1 concentration were observed in the whole blood to which pyridoxamine dihydrochloride was added. On the other hand, a decrease in the vitamin B1 concentration in a manner dependent on the concentration of pyridoxal hydrochloride was observed in the whole blood to which pyridoxal hydrochloride was added (Panel A of FIG. 4).

Sixteen hours after the incubation, a decrease in the vitamin B1 concentration was observed in the whole blood to which pyridoxamine dihydrochloride was added, compared with the baseline; however, this decrease was similar to that in the vehicle and was not considered to depend on addition of pyridoxamine. On the other hand, a decrease in the vitamin B1 concentration in a manner dependent on the concentration of pyridoxal hydrochloride was observed in the whole blood to which pyridoxal hydrochloride was added (Panel B of FIG. 4).

The above results clarified that pyridoxamine does not have the action of directly decreasing the whole blood vitamin B1 concentration, but that pyridoxal has the action of decreasing the whole blood vitamin B1 concentration.

In addition, as shown in Experiment Examples 1 and 2 above, since pyridoxamine is quickly metabolized to pyridoxal when absorbed in the body, it was predicted that pyridoxal, i.e., a metabolite, increased by administration of a pyridoxamine compound would decrease the vitamin B1 concentration in the body, resulting in a symptom of vitamin B1 deficiency.

Experiment Example 4

Prevention of Vitamin B1 Deficiency by Administration of Pyridoxamine Compound in Combination with Thiamine Compound On the basis of the results of the Experiment Examples above, it seemed necessary to prevent vitamin B1 deficiency when a carbonyl-stress-removing agent, such as pyridoxamine, is administered for schizophrenia or like AGE-related disease.

To investigate the effect of administering a pyridoxamine compound in combination with a thiamine compound, a thiamine compound was administered to seven schizophrenia patients (average age: 44.3 years old, average body weight: 55.4 kg) to which a pyridoxamine compound was to be administered, in parallel with administration of the pyridoxamine compound. More specifically, pyridoxamine dihydrochloride was used as a pyridoxamine compound and orally administered daily to each of the seven schizophrenia patients in an amount of 1200 to 1800 mg per day (administered in an amount of 400 to 600 mg three times a day) for 24 consecutive weeks. The dose of pyridoxamine dihydrochloride, i.e., 400 to 600 mg/one time, is 277 to 415 mg/one time when calculated as the dose of pyridoxamine. Fursultiamine was used as a thiamine compound. Oral administration of the thiamine compound in an amount of 75 mg/day was initiated from 2 to 21 weeks after the start of administration of the pyridoxamine compound, and then continued daily until the end of administration of the pyridoxamine compound.

The results showed that no findings suggestive of vitamin B1 deficiency were observed in any of the seven schizophrenia patients until the end of administration of the pyridoxamine compound.

From the results above, it was believed that when a pyridoxamine compound is administered in a relatively large amount, it is preferable to administer a thiamine compound in combination with the compound.

The invention claimed is:

1. A method for preventing and/or treating vitamin B1 deficiency in a subject, the method comprising administering
   (1) a therapeutically-effective amount of at least one pyridoxamine compound selected from the group consisting of pyridoxamine and pharmaceutically acceptable salts thereof, and
   (2) a therapeutically-effective amount of at least one thiamine compound, wherein the thiamine compound metabolizes to thiamine phosphate in the body,
   simultaneously or separately to a subject in need thereof, wherein the vitamin B1 deficiency is caused by administration of a pyridoxamine compound.

2. The method according to claim 1, wherein the daily dose of (1) the pyridoxamine compound is 300 mg or more, or 5 mg/kg body weight or more, calculated as pyridoxamine.

3. The method according to claim 1, wherein the daily dose of (1) the pyridoxamine compound is 600 mg or more, or 10 mg/kg body weight or more, calculated as pyridoxamine.

4. The method according to claim 1, wherein the subject has at least one disease selected from the group consisting of diabetes, diabetic complications, chronic renal failure, complications of chronic renal failure, nephropathy, nephritis, inflammatory diseases, atherosclerosis, age-related eye diseases, neurodegenerative diseases, alcoholism, autism, schizophrenia, malignant melanoma, deterioration of the peritoneum in peritoneal dialysis, chronic rheumatism, and atopic dermatitis.

5. The method according to claim 1, wherein the vitamin B1 deficiency is at least one disease or symptom selected from the group consisting of beriberi, axial optic neuritis, polyneuritis, Wernicke's encephalopathy, decreased appetite, and digestion disorders.

6. The method according to claim 1, wherein the therapeutically-effective amount of the at least one pyridoxamine compound is an amount sufficient to treat vitamin B1 deficiency in the subject.

* * * * *